(12) United States Patent
Fisher et al.

(10) Patent No.: US 10,155,807 B2
(45) Date of Patent: Dec. 18, 2018

(54) TREATING ALCOHOL-MEDIATED DISORDERS BY INHIBITION OF RGS6

(71) Applicant: UNIVERSITY OF IOWA RESEARCH FOUNDATION, Iowa City, IA (US)

(72) Inventors: Rory A. Fisher, Iowa City, IA (US); Biswanath Maity, Iowa City, IA (US); Adele M. Stewart, Iowa City, IA (US); David Roman, Iowa City, IA (US); Christopher R. Bodle, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/952,747

(22) Filed: Nov. 25, 2015

(65) Prior Publication Data

US 2016/0185843 A1 Jun. 30, 2016

Related U.S. Application Data

(60) Provisional application No. 62/085,137, filed on Nov. 26, 2014.

(51) Int. Cl.
*A61K 31/353* (2006.01)
*A61K 31/7088* (2006.01)
*C07K 16/18* (2006.01)
*C12N 15/113* (2010.01)

(52) U.S. Cl.
CPC ............ *C07K 16/18* (2013.01); *A61K 31/353* (2013.01); *A61K 31/7088* (2013.01); *C12N 15/113* (2013.01); *C07K 2317/76* (2013.01); *C12N 2310/11* (2013.01); *C12N 2310/14* (2013.01)

(58) Field of Classification Search
CPC .. A61K 31/353; A61K 31/7088; C07K 16/18; C07K 2317/76; C12N 2310/11; C12N 2310/14
See application file for complete search history.

(56) References Cited

U.S. PATENT DOCUMENTS

2014/0303199 A1 10/2014 Roman et al.

OTHER PUBLICATIONS

Ahlers, et al., "RGS6 as a Novel Therapeutic Target in CNS Diseases and Cancer", AAPS Journal, vol. 18(3), 560-572 (2016).
Monroy, et al., "A high throughput screen for RGS proteins using steady state monitoring of free phosphate formation", PLoS One 8(4), 362247 (2013).
Stewart, et al., "Regulator of G protein signaling 6 is a critical mediator of both reward-related behavioral and pathological responses to alcohol", Proc Natl Acad Sci 112(7), E786-795 (2015).
Hsieh, et al., "Brazilein suppresses migration and invasion of MDA-MB-231 breast cancer cells", Chemico-Biological Interactions 204, 105-115 (2013).
Lan, et al., "Determination of brazilein in rat plasma after intravenous administration by HPLC", Biomedical chromatography 22, 1201-1205 (2008).
Li, et al., "Effect of brazilein on energy metabolism of cerebral ischemia-reperfusion in mice", Chinese Journal of Chinese Materia Medica vol. 35(18), 2448-2452 (2010).
Sasaki, et al., "In Vitro Study for Inhibition of NO Production about Constituents of Sappan Lignum", Biol Pharm Bull 30(1), 193-196 (2007).
Shen, et al., "Brazilein-induced contraction of rat arterial smooth muscle involves activation of Ca2+ entry and ROK, ERK pathways", European Journal of Pharmacology 580, 366-371 (2008).
Tao, et al., "Brazilein, a compound isolated from Caesalpinia sappan Linn., induced growth inhibition in breast cancer cells via involvement of GSK-3β/β-Catenin/cyclin D1 pathway", Chemico-Biological Interactions 206, 1-5 (2013).
Yan, et al., "Development and optimization of a method for the analysis of Brazilein by HPLC with electrochemical detection", Journal of Chromatography A, 1077, 44-48 (2005).
Zhao, et al., "Study on Cardioactive Effects of Brazilein", Pharmacology 76, 76-83 (2006).

*Primary Examiner* — Robert S Landsman
*Assistant Examiner* — Bruce D. Hissong
(74) *Attorney, Agent, or Firm* — Viksnins Harris Padys Malen LLP

(57) ABSTRACT

The invention provides RGS6 antagonists and methods for their use in treating the effects of alcohol consumption.

1 Claim, 18 Drawing Sheets

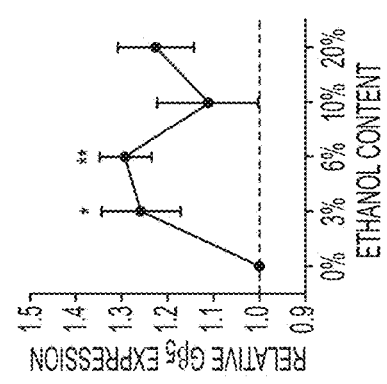
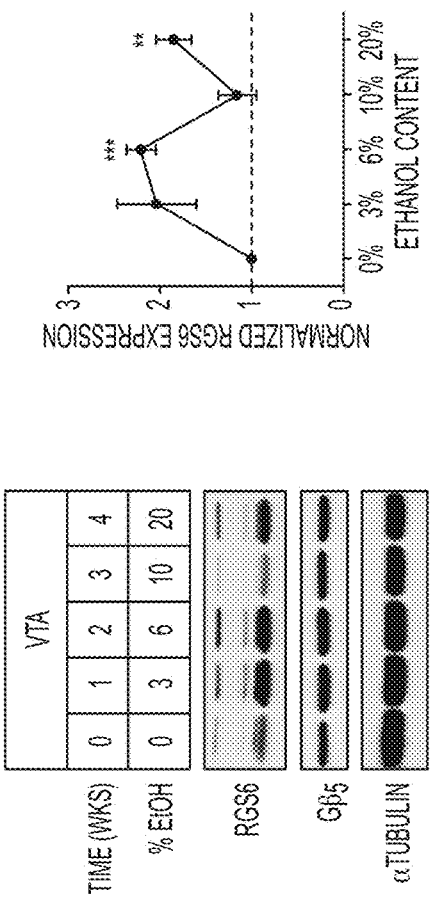
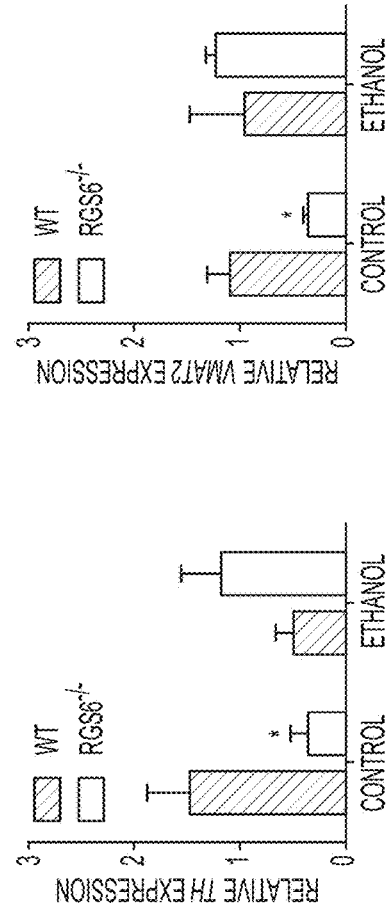
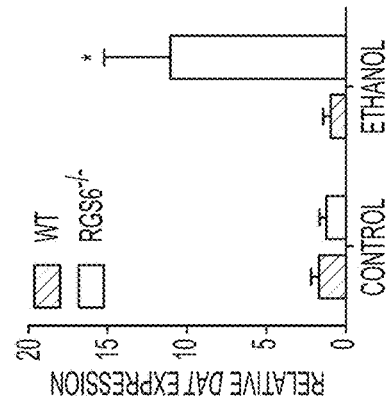
FIG. 2B
FIG. 2C

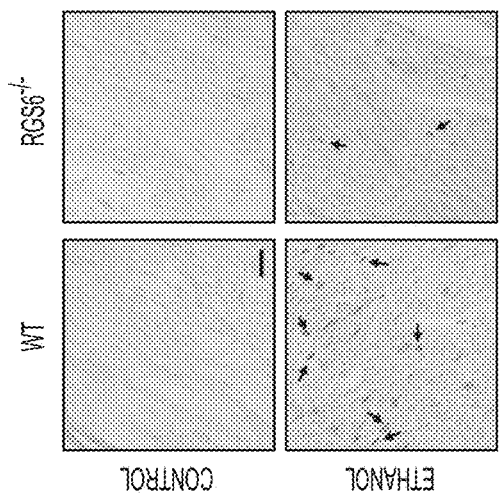
FIG. 4A
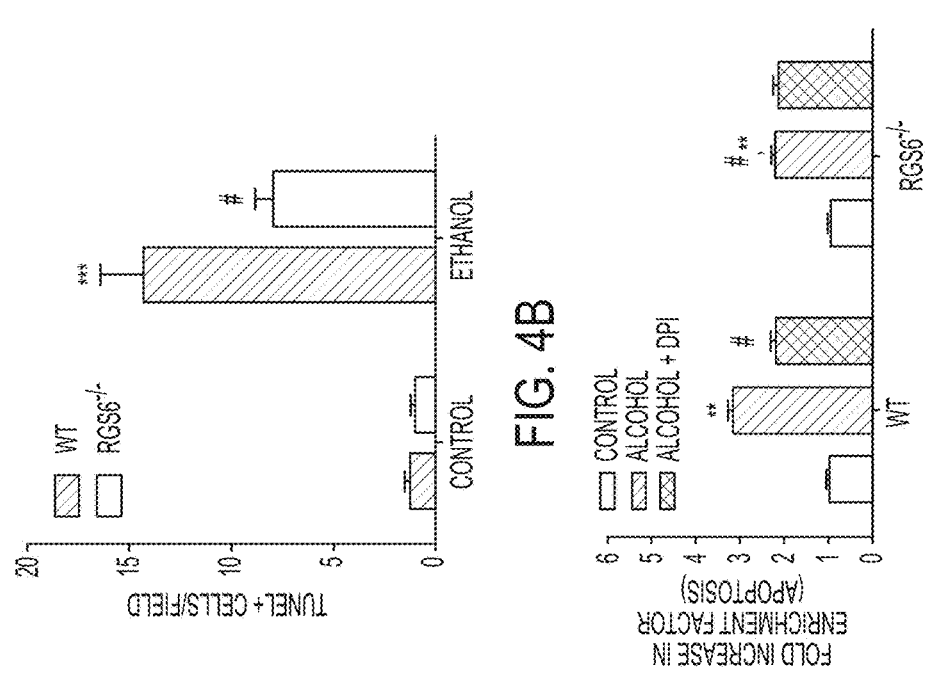
FIG. 4B
FIG. 4C
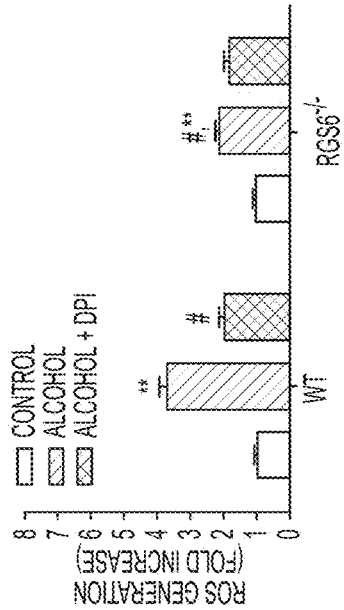
FIG. 4D

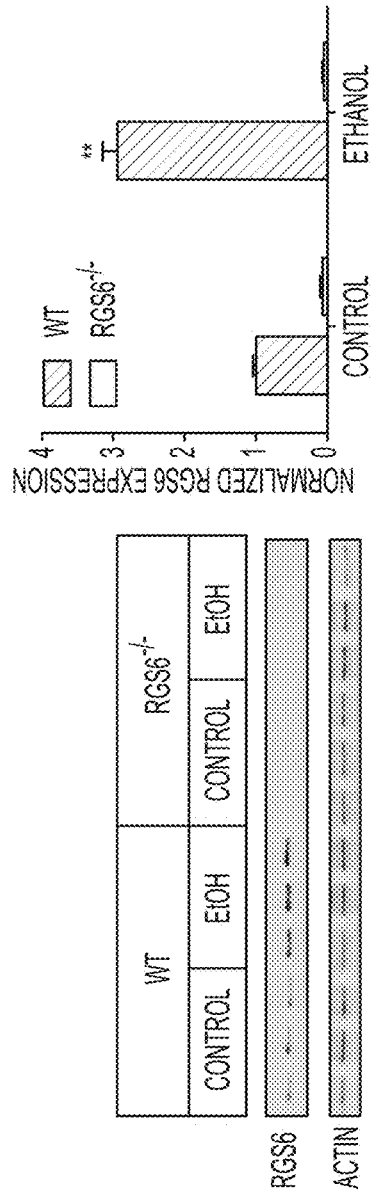
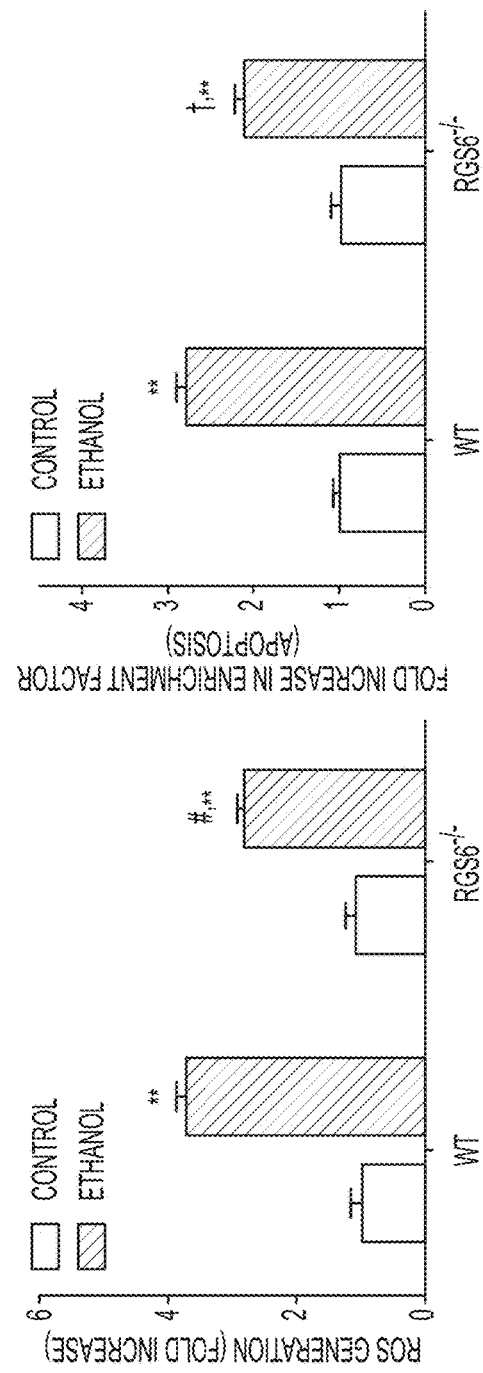
FIG. 6C
FIG. 6D
FIG. 6E

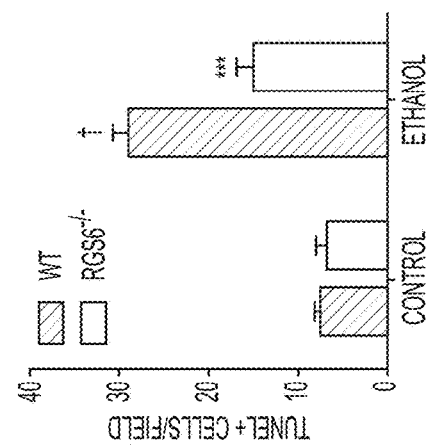
FIG. 7A
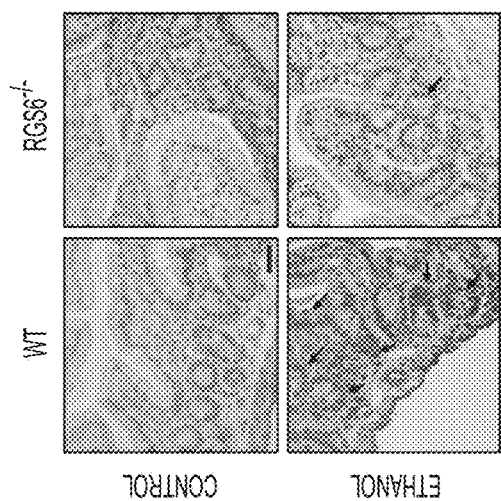
FIG. 7B
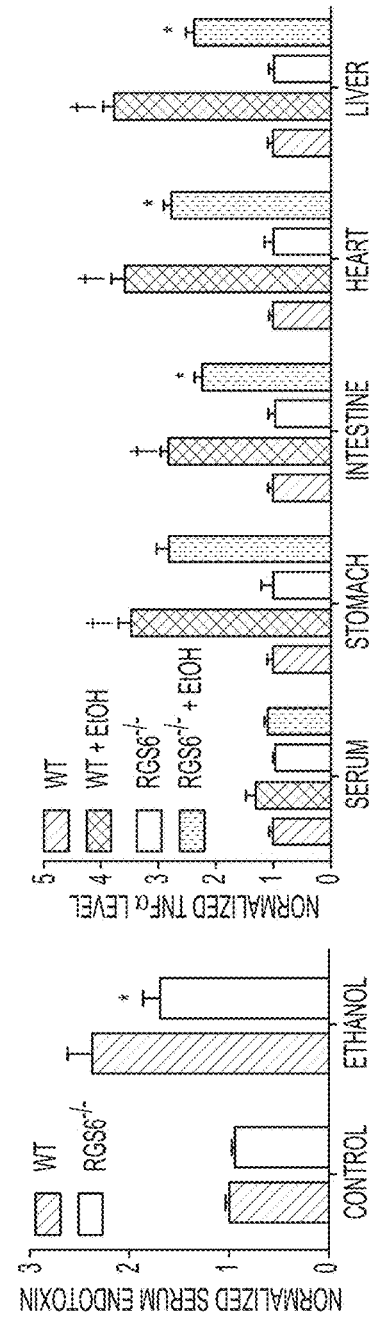
FIG. 7C
FIG. 7D

TREATING ALCOHOL-MEDIATED DISORDERS BY INHIBITION OF RGS6

CROSS-REFERENCE TO RELATED APPLICATION(S)

This patent application claims the benefit of priority of U.S. application Ser. No. 62/085,137, filed Nov. 26, 2014, which application is herein incorporated by reference.

STATEMENT OF GOVERNMENT SUPPORT

This invention was made with government support under CA161882 awarded by the National Institutes of Health. The government has certain rights in the invention.

BACKGROUND

Alcoholism imparts a large socioeconomic burden on the healthcare system in the United States, affecting an estimated 12% of the population, a prevalence greater than that for all other drugs of abuse combined. Despite decades of research, our understanding of the mechanisms underlying the acquisition of alcohol dependence remains limited. As a result, there are few currently approved therapeutics designed to reduce alcohol cravings or withdrawal symptomology, and abstinence remains the only effective way to prevent the tissue damage that results from chronic alcohol abuse. As such, treatments designed to reduce alcohol cravings or ameliorate tissue damage resulting from chronic alcohol abuse are needed.

SUMMARY OF CERTAIN EMBODIMENTS

Certain embodiments of the present invention provide methods of treating the neurobiological/behavioral and tissue damaging effects of alcohol consumption in an individual in need of such treatment, comprising administering to the individual an effective amount of an antagonist of Regulator of G protein Signaling 6 (RGS6).

In certain embodiments, the treatment reduces alcohol cravings and/or alcohol withdrawal.

In certain embodiments, the treatment decreases alcohol-mediated organ damage.

In certain embodiments, the organ is the heart, stomach, intestine or liver.

In certain embodiments, the treatment decreases alcohol-mediated cardiac, gastrointestinal and/or hepatic damage.

In certain embodiments, the treatment decreases alcohol-mediated cardiac damage.

In certain embodiments, the treatment decreases alcohol-mediated gastrointestinal damage.

In certain embodiments, the treatment decreases alcohol-mediated hepatic damage

In certain embodiments, the damage is cardiomyopathy, hepatic cirrhosis, or alcohol-induced gastric barrier dysfunction.

In certain embodiments, the treatment reduces alcohol dependence.

In certain embodiments, the antagonist is a small molecule antagonist.

In certain embodiments, the antagonist is siRNA.

In certain embodiments, the antagonist is antisense and inhibitory RNA (e.g., siRNA, shRNA) delivered, e.g., by injection or virus.

In certain embodiments, the antagonist is an antibody.

Certain embodiments of the invention provide methods to treat alcohol seeking behavior, dependence, and/or withdrawal.

Certain embodiments provide methods to prevent further pathological effects of alcohol dependence on the gastrointestinal track, heart, and/or liver.

Certain embodiments provide methods to treat other addictive behaviors (e.g., cannabinoid addiction).

Certain embodiments provide methods to treat tachycardia.

Certain embodiments provide methods to regulate the $GABA_BR$.

BRIEF DESCRIPTION OF THE FIGURES

(FIG. 1A) EtOH consumption in free choice and forced phases of the experiment normalized to body weight (g EtOH/kg body weight/day) and (FIG. 1B) EtOH preference are shown. (FIG. 1C) EtOH consumed by WT (n=14) and $RGS6_{-/-}$ mice (n=14) given free access to increasing concentrations of EtOH containing solutions (3%, 6%, 10%, 20%) for one week each. EtOH withdrawal severity in WT (n=9) and $RGS6_{-/-}$ mice (n=9) as depicted by (FIG. 1D) hourly handling induced convulsions (HIC) score and (FIG. 1E) area under the curve from figure d. (FIG. 1F) Time spent by WT (n=9) and RGS6−/− (n=8) mice in the EtOH box during the testing phase of the conditioned place preference paradigm. (FIG. 1G) Duration of the loss of righting reflex (LORR) in EtOH-treated WT (n=8) and $RGS6_{-/-}$ (n=9) mice. (FIG. 1H) $RGS6_{-/-}$ mice were less sensitive to the ataxic effects of alcohol on the rotarod as measured by the change in rotarod speed at which each mouse fell before and after EtOH treatment. Both WT (n=6-8) and $RGS6_{-/-}$ (n=6-9) mice were tested in the short-term alcohol consumption paradigm. EtOH consumption in free choice phase of the experiment is depicted normalized to body weight (gEtOH/kg body weight/day). (FIG. 1I) Treatment with SCH-50911 partially reversed the reduction in alcohol consumption observed in $RGS6^{-/-}$ mice. *, P<0.05; , P<0.01; *, P<0.001 vs. WT and #, P<0.05 vs $RGS6_{-/-}$ controls by student's t-test (single variable) or ANOVA with the Bonferroni post-hoc adjustment (multi-variable). Data are presented as mean±S.E.M.

FIG. 2A-2C. RGS6, up-regulated in the VTA of alcohol-consuming mice, regulates genes involved in dopamine bioavailability. (FIG. 2A) IHC staining of RGS6 expression in the VTA of WT and $RGS6_{-/-}$ mice. TH is used as a marker of dopaminergic neurons. DAPI was used to stain the nuclei [scale bar=20 μm; white boxes, regions shown in enlarged images]. (FIG. 2B) RGS6 and $G\beta_5$ immunoblots in the VTA of WT mice given free access to graduated alcohol containing solutions (0-20%) for increasing periods of time (Left panel). Densitometric quantification was performed with protein levels (n=3) normalized to tubulin loading control and expressed relative to control conditions (Right panels). (FIG. 2C) DAT, TH, and VMAT2 mRNA expression in the VTA of WT (n=3-6) and $RGS6_{-/-}$ mice (n=3-6) fed on an isocaloric control or EtOH (5%) containing Liber deCarli liquid diet for 2 months. *, P<0.05; **, P<0.01 vs WT control by ANOVA with the Bonferroni post-hoc adjustment. Data are presented as mean±S.E.M.

(FIG. 3A) RGS6 expression in the heart of WT mice given free access to graduated alcohol containing solutions (0-20%) for increasing periods of time (Left panel). Densitometric quantification was performed with protein levels (n=3) normalized to actin loading control and expressed relative to control conditions (Right panels). Animals (WT, n=8-10; RGS6−/−, n=8-10) were fed on 5% EtOH containing or isocaloric maltose dextrin Lieber deCarli liquid diet for 2 months. At the end of the treatment regimen (FIG. 3B) heart weight was measured (WT, n=8-10; $RGS6_{-/-}$, n=7-10) and (FIG. 3C) Masson Trichrome (fibrotic remodeling), and (FIG. 3D) H & E staining were performed. Black arrows indicate areas of microfilament disarray in the H & E stained sections. Images are representative of at least 3 independent experiments [scale bar=100 μm].*, $P<0.05$ and #, $P<0.01$ vs. WT EtOH-treated samples by ANOVA with the Bonferroni post-hoc adjustment. Data are presented as mean±S.E.M.

FIG. 4A-4D. RGS6 promotes cardiomyocyte apoptosis by facilitating Nox-dependent ROS generation. Animals (WT, n=8-10; $RGS6_{-/-}$, n=8-10) were fed on 5% EtOH containing or isocaloric maltose dextrin Lieber deCarli liquid diet for 2 months. At the end of the treatment regimen (FIG. 4A) TUNEL staining was performed. Black arrows indicate apoptotic cells in the TUNEL stained sections. Images are representative of at least 3 independent experiments [scale bar=100 μm]. TUNEL positive cells were quantified from 10 random microscope fields in (FIG. 4B) (FIG. 4C) ROS generation ($CM-H_2$-DCFDA fluorescence) was measured in neonatal VCM isolated from WT and $RGS6_{-/-}$ mice (n=4) and treated with alcohol following pre-treatment with DPI to inhibit Nox. (FIG. 4D) VCM were treated as in b (n=3) and apoptosis measured.*, $P<0.05$; , $P<0.01$; *, $P<0.001$ vs WT controls and #, $P<0.01$ vs. WT EtOH-treated samples by ANOVA with the Bonferroni post-hoc adjustment. Data are presented as mean±S.E.M.

(FIG. 5A) RGS6 expression in the liver of WT mice given free access to graduated alcohol containing solutions (0-20%) for increasing periods of time (Left panel). Densitometric quantification was performed with protein levels (n=3) normalized to actin loading control and expressed relative to control conditions (Right panels). Animals (WT, n=8-10; $RGS6_{-/-}$, n=8-10) were fed on 5% EtOH containing or isocaloric maltose dextrin Lieber deCarli liquid diet for 2 months. At the end of the treatment regimen (FIG. 5B) liver weight (WT, n=8-10; $RGS6_{-/-}$, n=7-10) was measured and (FIG. 5C) Oil Red 0 (fatty acid deposition), and (FIG. 5D) H & E were performed. Black arrows indicate areas of macrovesicular hepatic steatosis in the H & E stained sections. Images are representative of at least 3 independent experiments [scale bar=100 μm]. Plasma (FIG. 5E) AST, (FIG. 5F) ALT, and (FIG. 5G) triglycerides were measured in WT (n=6) and $RGS6_{-/-}$ mice (n=6-10) following the 2 month alcohol feeding regimen. *, $P<0.05$; **, $P<0.01$ vs WT controls and #, $P<0.01$ vs. WT EtOH treated samples by ANOVA with the Bonferroni post-hoc adjustment. Data are presented as mean±S.E.M.

FIG. 6A-6E. Alcohol-induced hepatic ROS generation and apoptosis is reduced in $RGS6_{-/-}$ hepatocytes. (FIG. 6A) Animals (WT, n=8-10; $RGS6_{-/-}$, n=8-10) were fed on 5% EtOH containing or isocaloric maltose dextrin Lieber deCarli liquid diet for 2 months. At the end of the treatment regimen TUNEL staining was performed. Black arrows indicate apoptotic cells in the TUNEL stained sections. Images are representative of at least 3 independent experiments [scale bar=100 μm]. TUNEL positive cells were quantified from 11 random microscope fields in (FIG. 6B). (FIG. 6C) RGS6 expression in the hepatocytes of alcohol treated WT and $RGS6_{-/-}$ hepatocytes (top panel). Densitometric quantification was performed with protein levels (n=3) normalized to actin loading control and expressed relative to control conditions (bottom panel). (FIG. 6D) ROS generation ($CM-H_2$-DCFDA fluorescence) was measured in hepatocytes isolated from WT and $RGS6_{-/-}$ mice (n=3-4) and treated with alcohol. (FIG. 6E) Apoptosis was measured in lysates from WT and $RGS6_{-/-}$ hepatocytes (n=3-4) treated with alcohol and expressed as the fold increase in cytoplasmic histone-associated DNA fragments (enrichment factor). *, $P<0.05$; , $P<0.01$; *, $P<0.001$ vs WT alcohol treated cells and #, $P<0.05$; †, $P<0.01$ vs. WT control samples by ANOVA with the Bonferroni post-hoc adjustment. Data are presented as mean±S.E.M.

FIG. 7A-7D. RGS6 deficiency ameliorates alcohol-induced gastrointestinal dysfunction. Animals (WT, n=8; $RGS6_{-/-}$, n=8) were treated EtOH according to a 3 dose acute protocol. At the end of the treatment regimen (FIG. 7A) TUNEL staining [scale bar=50 μm] was performed in intestine. Black arrows indicate large clusters of apoptotic cells in TUNEL stained sections. Images are representative of at least 3 independent experiments. TUNEL positive cells were quantified from 10 random microscope fields in (FIG. 7B). (FIG. 7C) Serum endotoxin levels (WT, n=3-8; $RGS6_{-/-}$, n=3-8) and (FIG. 7D) serum, liver, stomach, intestine and heart TNFα levels (WT, n=3; $RGS6_{-/-}$, n=3) were measured in WT and $RGS6_{-/-}$ mice following 1 month of EtOH exposure (5% Lieber deCarli liquid diet). *, $P<0.05$; ***, $P<0.001$ vs. EtOH-treated WT samples by ANOVA with the Bonferroni post-hoc adjustment; #, $P<0.05$ vs WT control via student's t-test; and †, $P<0.001$ vs WT control by ANOVA with the Bonferroni post-hoc adjustment. Data are presented as mean±S.E.M.

(FIG. 8A) Results indicated that, by inhibiting $GABA_BR$ signaling, RGS6 promotes alcohol seeking behaviors. As a result, deletion of RGS6, normally up-regulated by ethanol in the VTA, ameliorates alcohol reward and withdrawal likely by impacting dopamine bioavailability required for the reinforcing effects of drugs of abuse. (FIG. 8B) At the same time, RGS6 normally functions to promote the cytotoxic actions of ethanol in the heart and liver though multiple mechanisms. First, in VCM, RGS6 promotes Nox-dependent ROS generation to facilitate alcohol-induced cell loss and also hypertrophy and fibrosis. In hepatocytes, RGS6 increases apoptosis and ROS generation and also increases the expression of genes involved in fatty acid synthesis leading to hepatic steatosis and compromised liver function after EtOH exposure. Finally, RGS6 also promotes apoptosis in the gut epithelium that contributes to intestinal leakage leading to the release of endotoxin and the inflammatory cytokine TNFα into the peripheral circulation. Thus, singular deletion of the RGS6 gene is sufficient to reduce alcohol seeking behaviors, reward, and withdrawal while at the same time protecting the animal from the cardiac, hepatic and gastrointestinal damage that normal results from chronic alcohol consumption.

FIG. 9A. If no ppi is occurring, the singlet oxygen does not reach the acceptor bead and no light is produced. FIG. 9B. If a ppi is occurring, the singlet oxygen reacts with thioxene derivatives within the acceptor bead and light is produced at 520-620 nm.

DETAILED DESCRIPTION

Figure 1C:
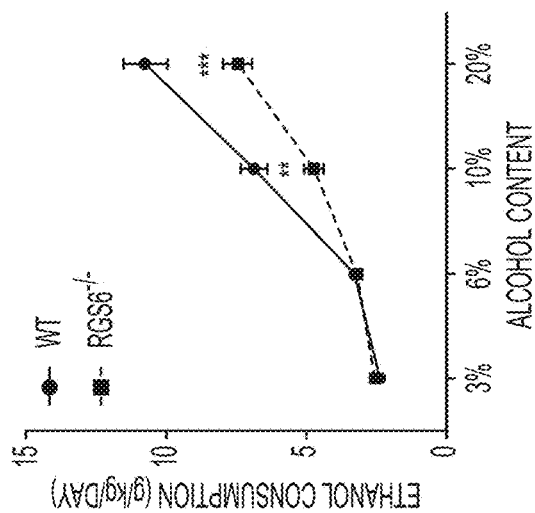
FIG. 1A-1I. RGS6 deficiency reduces alcohol consumption, withdrawal, and reward without impacting sedation and ataxia. WT (n=12) and $RGS6_{-/-}$ (n=11) mice were tested in the short-term two bottle free choice alcohol consumption paradigm.
Figure 1B:
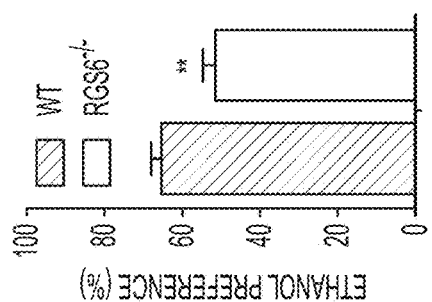
Figure 1A:
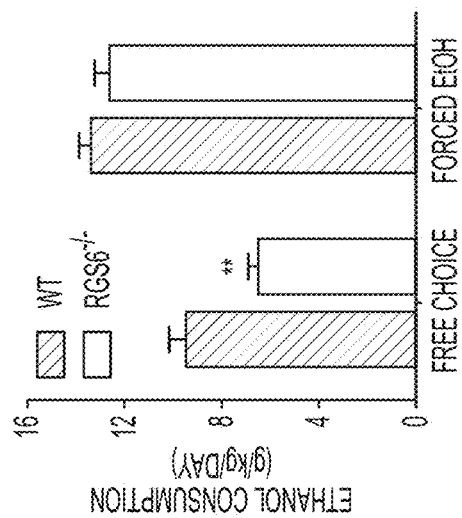
Figure 1F:
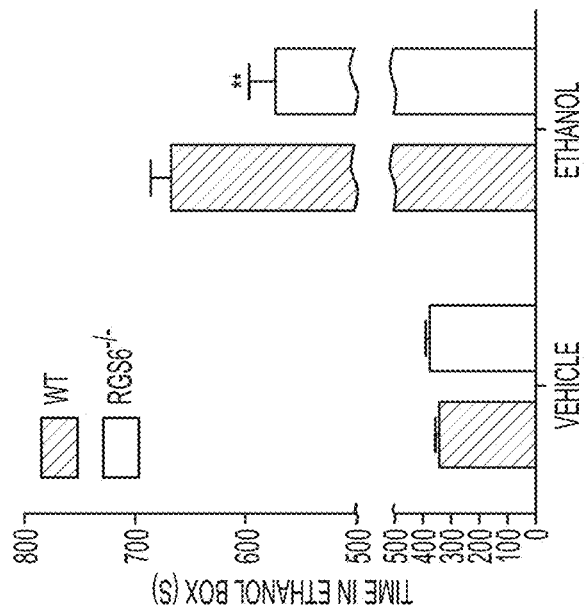
Figure 1E:
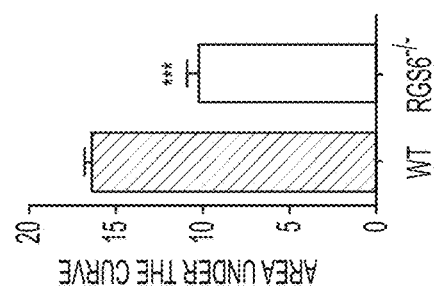
Figure 1D:
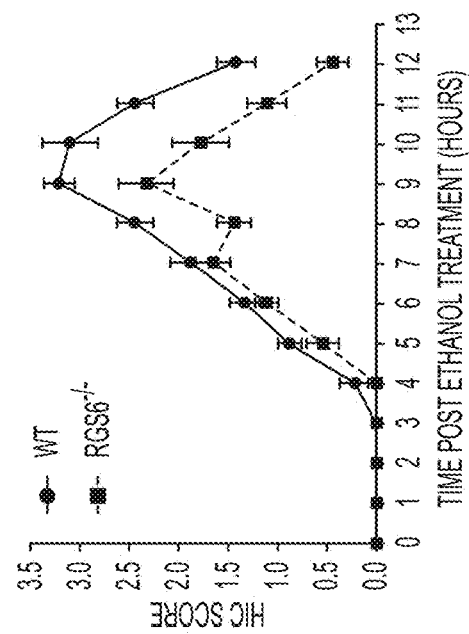
Figure 1I:
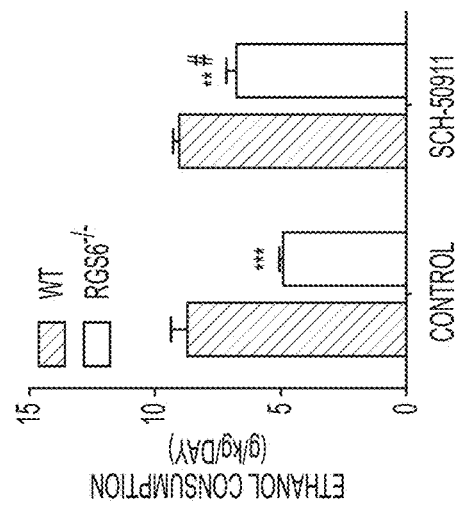
Figure 1H:
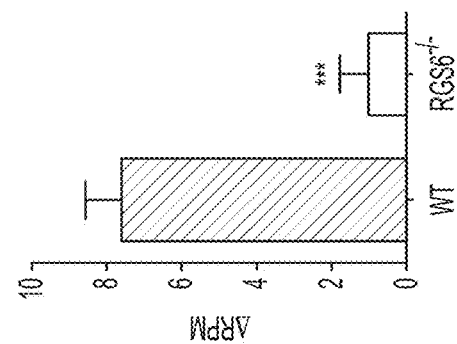
Figure 1G:
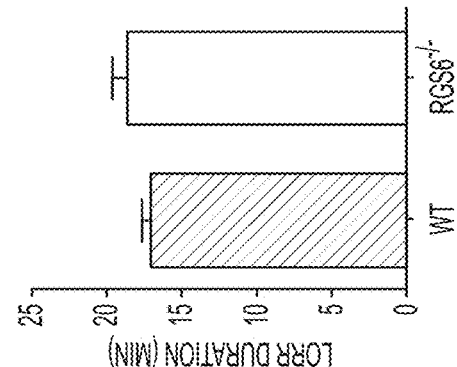
Figure 2A:
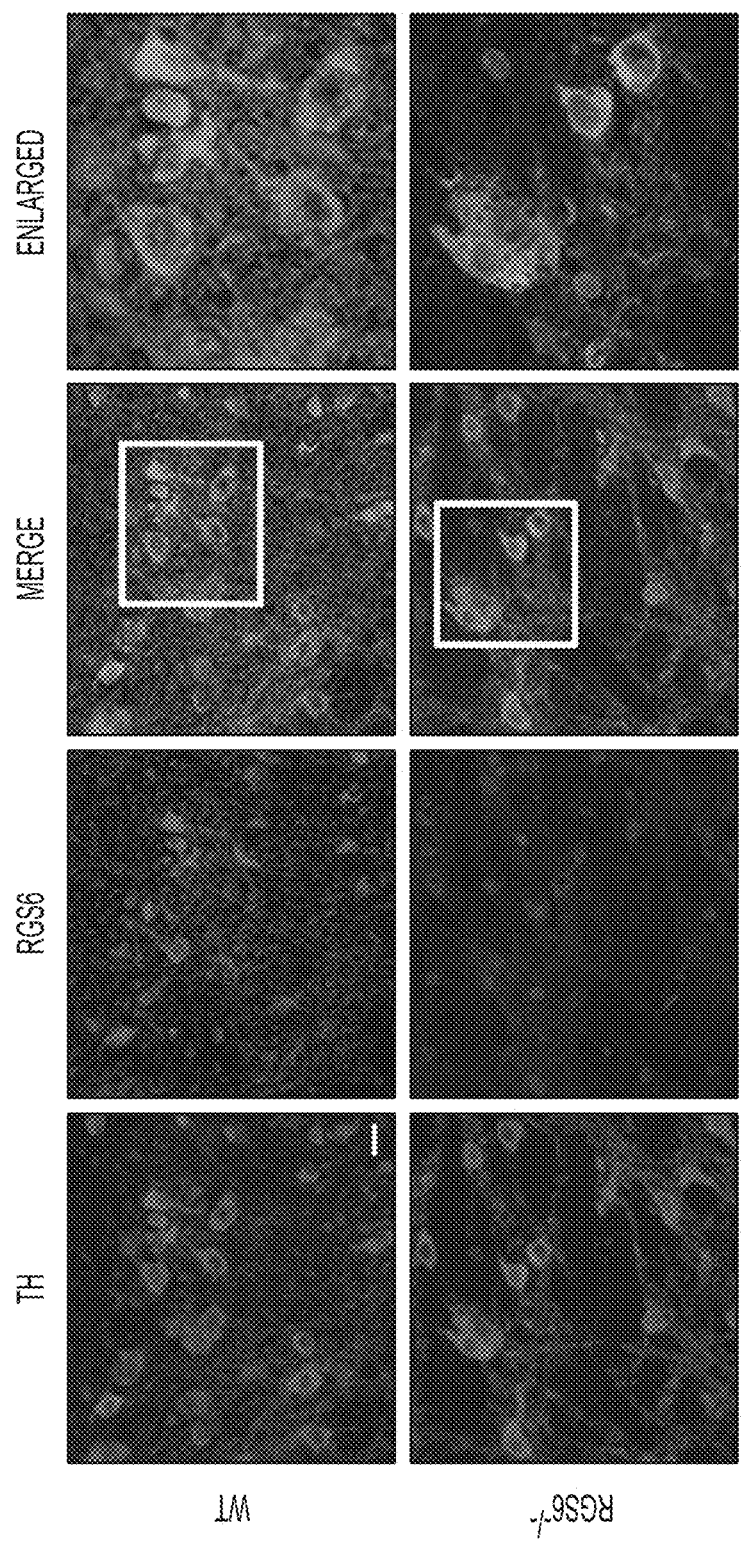
Figure 3A:
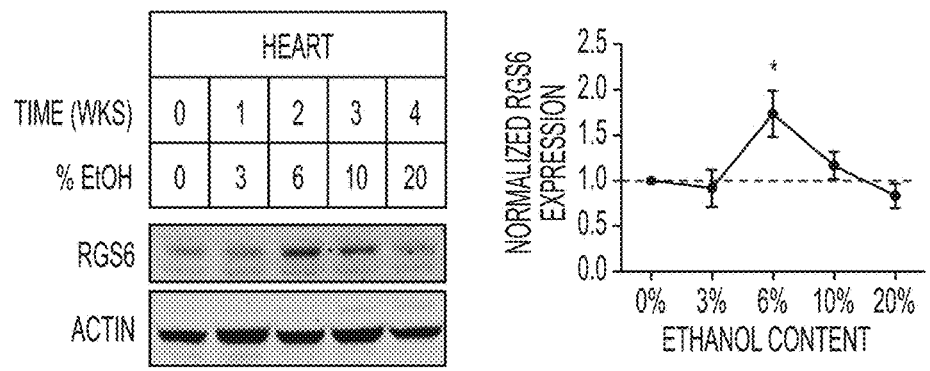
FIG. 3A-3D. RGS6 deficiency protects mice from alcoholic cardiomyopathy.
Figure 3B:
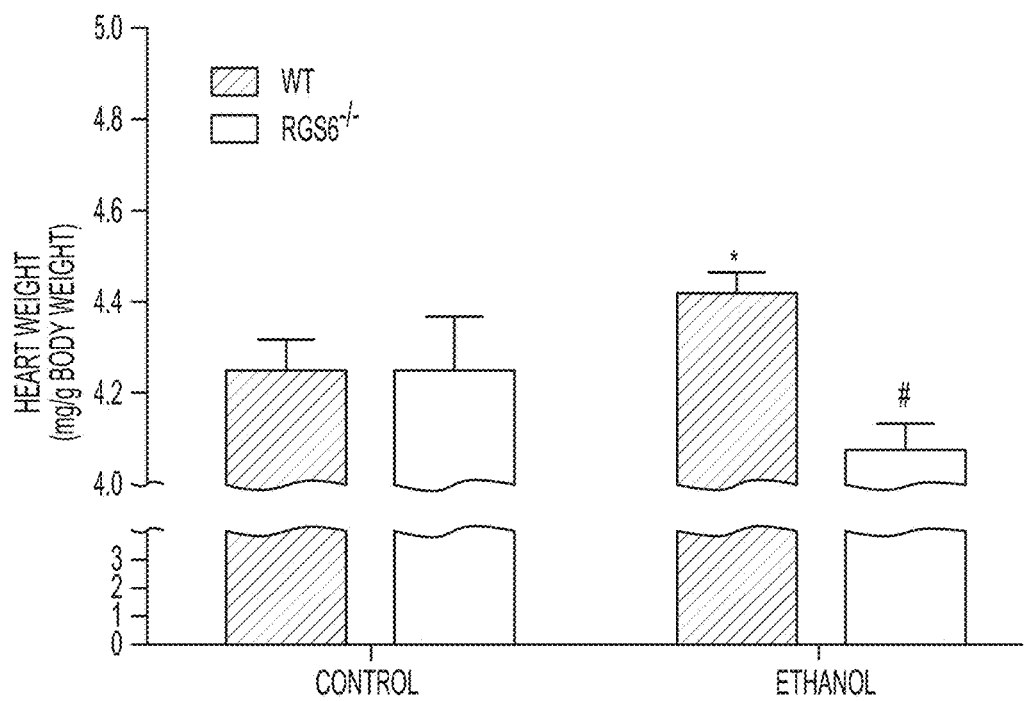
Figure 3D:
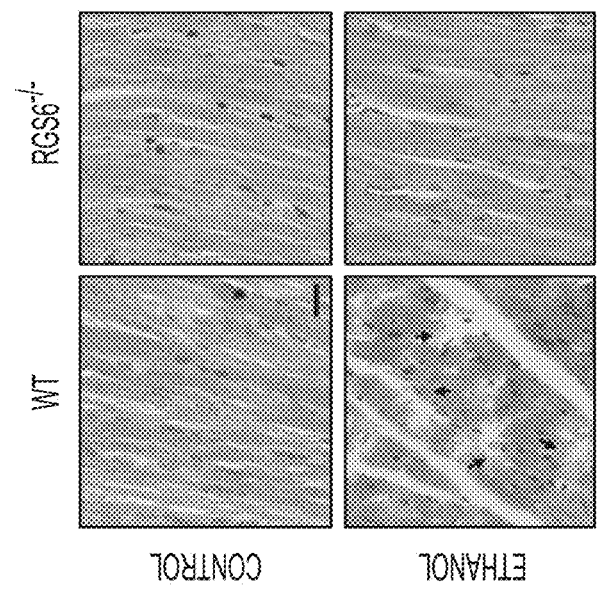
Figure 3C:
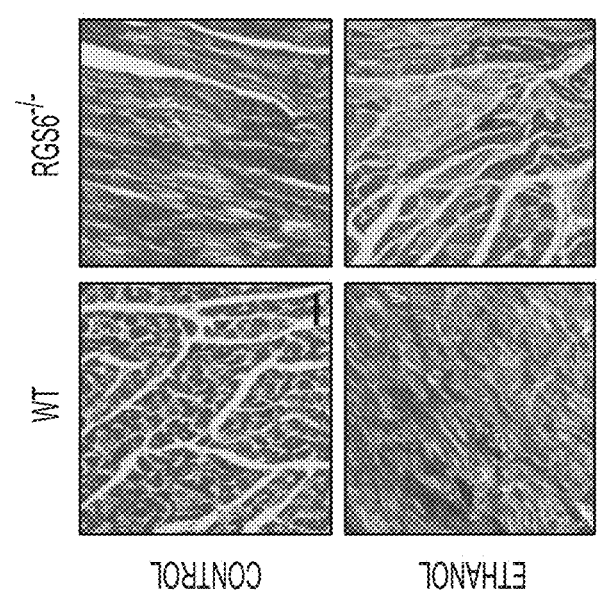
Figure 5A:
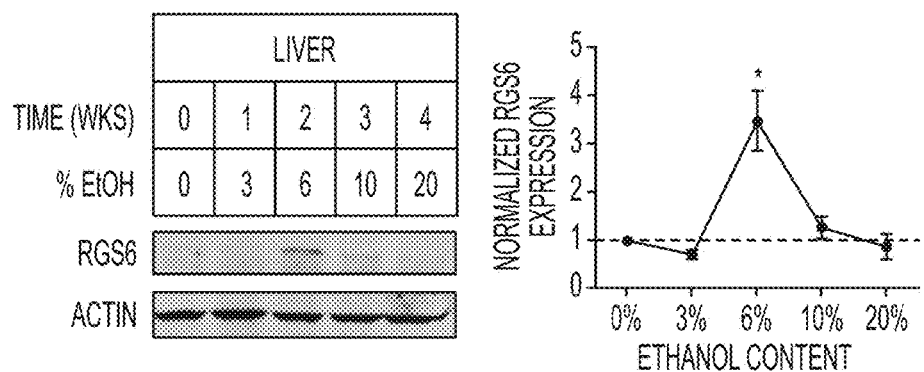
FIG. 5A-5G. $RGS6_{-/-}$ mice are protected against alcoholic hepatic steatosis.
Figure 5B:
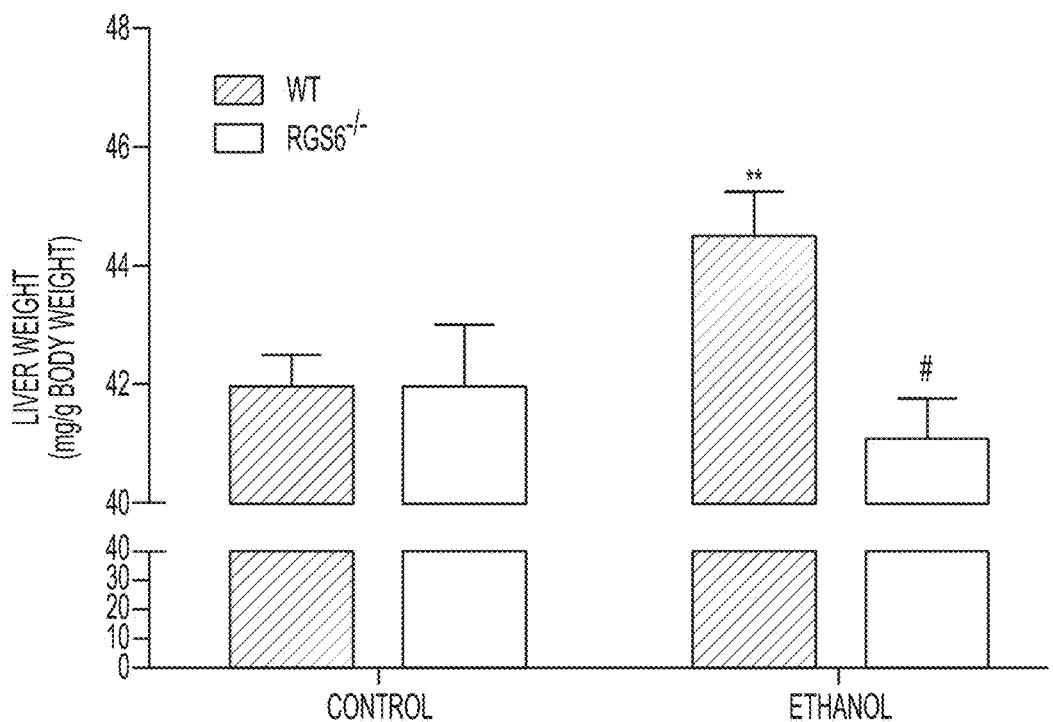
Figure 5C:
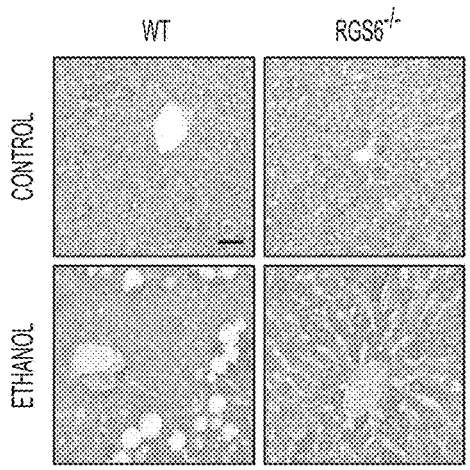
Figure 5D:
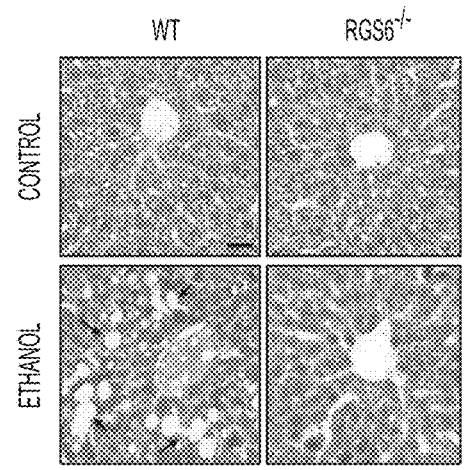
Figure 5E:
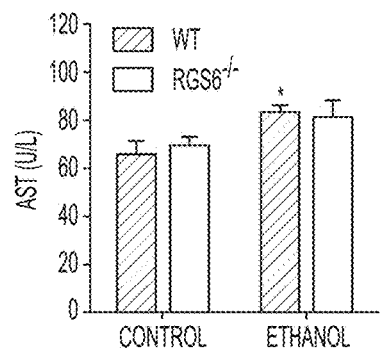
Figure 5F:
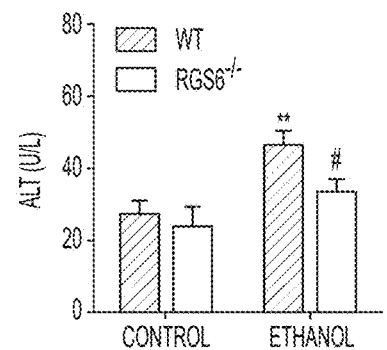
Figure 5G:
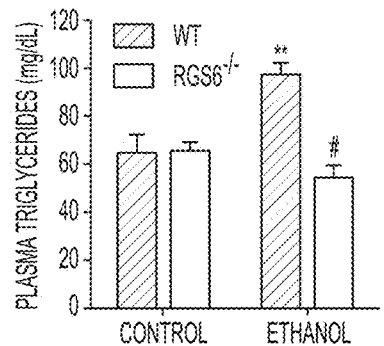
Figure 6A:
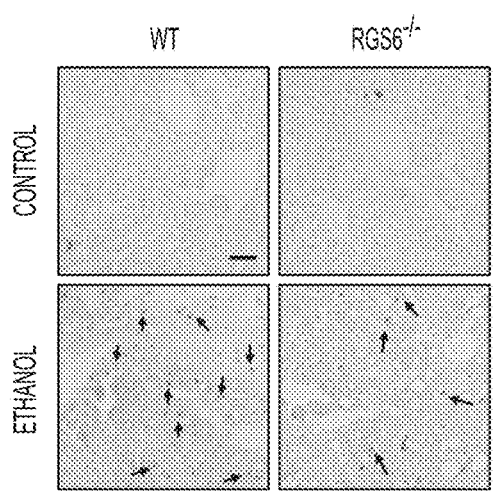
Figure 6B:
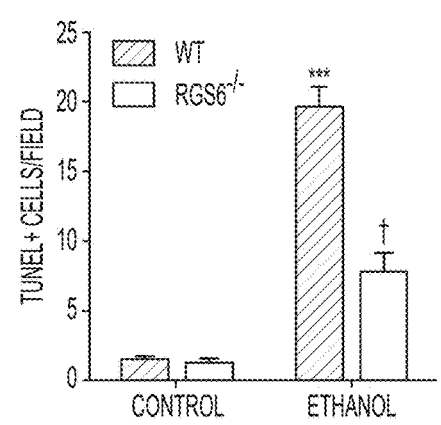
Figure 8A:
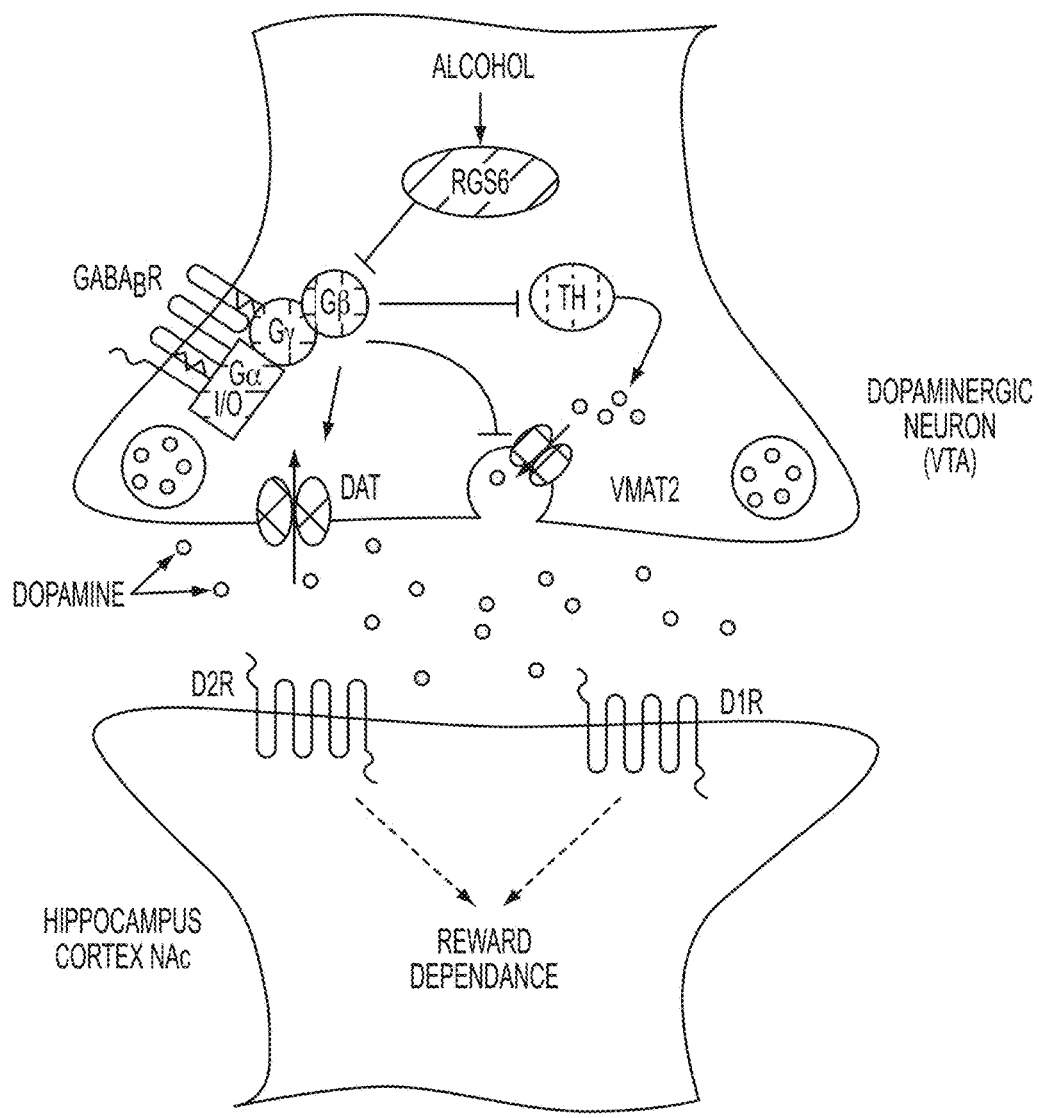
FIG. 8A-8B. Schematic outlining the role of RGS6 in alcohol seeking behaviors and the resultant cardiac, hepatic and gastrointestinal damage.
Figure 8B:
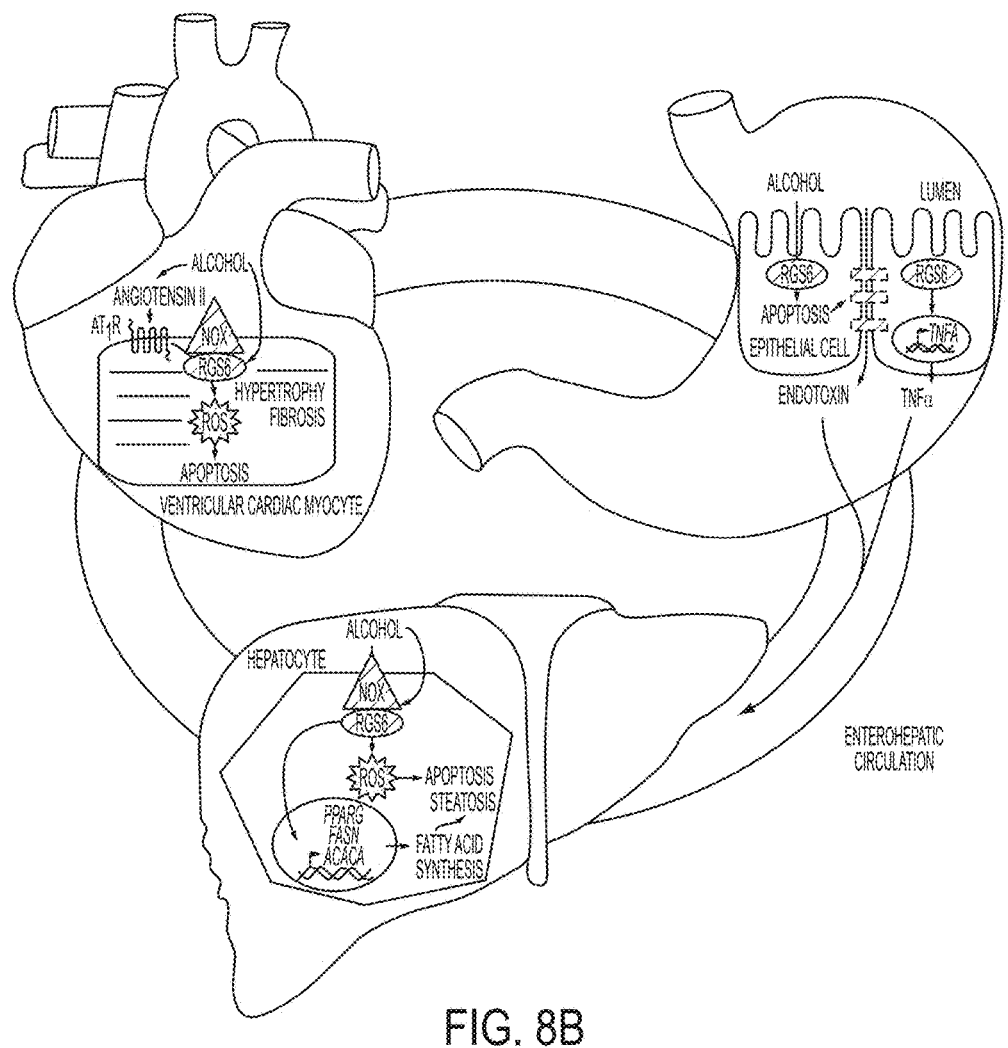

Alcohol is the most commonly abused drug worldwide, and chronic alcohol consumption is a major etiological factor in the development of multiple pathological sequelae including alcoholic cardiomyopathy and hepatic cirrhosis. As described herein, Regulator of G protein Signaling 6 (RGS6) has been discovered to be a critical regulator of both alcohol seeking behaviors as well as the associated cardiac and hepatic morbidities through two mechanistically divergent signaling actions. Mice lacking RGS6 consume less alcohol when given free access and are less susceptible to alcohol-induced reward and withdrawal. These actions appear to be due to potentiation of γ-Aminobutyric acid receptor B (GABA$_B$R) activity and associated with dysregulation of dopamine homeostasis in the ventral tegmental area (VTA), a population of dopaminergic neurons in the mesolimbic circuit heavily implicated in reinforcing the addictive properties of drugs of abuse. In heart, liver and gastrointestinal tract RGS6 promotes reactive oxygen species (ROS)-dependent apoptosis. As a result, loss of RGS6 provides dramatic protection against cardiac hypertrophy and fibrosis, hepatic steatosis, and gastrointestinal barrier dysfunction and endotoxemia. RGS6 is a targetable protein product mediating the behavioral actions of alcohol as well as the only molecule identified whose loss protects against alcohol induced hepatic steatosis, cardiomyopathy (including fibrosis) and gastrointestinal damage. Thus, inhibition of RGS6 represents a viable means to reduce alcohol cravings and withdrawal in human patients while simultaneously protecting the heart and liver from further damage upon relapse.

Alcohol Dependence

Alcohol dependence is a progressive, neurodevelopmental disorder characterized by accumulating neuroadaptations resulting from exposure to increasingly higher doses of ethanol (EtOH) over time. Both the acute intoxicating effects and long-term addictive properties of alcohol are believed to arise through a dynamic interplay between the actions of EtOH at the synaptic, neuronal, and neural circuit levels. Unlike many drugs of abuse, no specific molecular target of EtOH has been identified. Instead, EtOH functions as a central nervous system depressant through its ability to simultaneously dampen excitatory neurotransmission mediated by N-methyl-D-aspartate (NMDA) subtype glutamate receptors and enhance inhibitory neurotransmission through inotropic γ-aminobutyric acid type A receptors (GABA$_A$Rs). Alcohol also promotes acute neurotransmitter aberrations and chronic neural adaptations in the mesolimbic neuronal circuit, a major dopaminergic pathway in the brain implicated in drug addiction. This system includes the dopaminergic neurons of the ventral tegmental area (VTA), GABAergic neurons of the nucleus accumbens (NAc), and their efferent targets in the amygdala, hippocampus and medial pre-frontal cortex.

The neurotransmitters that facilitate neuronal communication in the mesolimbic pathway (e.g. dopamine; γ-Aminobutyric acid, GABA) bind to and activate a variety of G protein-coupled receptors (GPCRs) located on pre- and post-synaptic neurons. Susceptibility to alcohol abuse has been associated with genetic variants in the receptors for dopamine and GABA as well as those for endogenous opioids and serotonin all of which act through GPCRs. Clearly, novel mechanistic insight into the GPCR-regulated processes underlying alcohol dependence could facilitate the development of novel effective therapeutics.

By facilitating inactivation of the heterotrimeric G protein complex, Regulators of G protein Signaling (RGS) proteins serve as gatekeepers of the cellular response to GPCR activation. Receptors for the neurotransmitters mentioned above couple to G$\alpha_{i/o}$ and thus may be subject to negative regulation by one particular member of the RGS protein superfamily, RGS6. RGS6 has been identified as a critical negative regulator of the G$\alpha_{i/o}$-coupled GABA$_B$Rs and 5-HT$_{1A}$Rs, respectively (Maity et al., J Biol Chem. 2012; 287(7):4972-81; Stewart et al., FASEB J. 2014). No studies have investigated the role of RGS proteins in alcohol dependence.

EtOH consumption is a major etiologic factor in the development of additional pathological sequelae with significant associated morbidity and mortality including non-ischemic dilated cardiomyopathy and chronic liver disease that progresses from fatty liver to hepatitis, cirrhosis and eventual organ failure. It is estimated that 1 in 10 deaths in working age adults result from excess alcohol consumption. While a majority of the mortality associated with alcohol drinking can be attributed to accidents, a substantive portion results from the long-term consequences of alcohol exposure including heart and liver disease. Interestingly, the mechanisms underlying these distinct pathologies both involve the accumulation of reactive oxygen species (ROS) that contribute to cell death, inflammation, fibrotic remodeling, and loss of tissue functional integrity. Though the exact pathogenic ROS source remains unclear, scavenging or inhibition of superoxide anion generation from activated NADPH oxidase (Nox) complexes protects against EtOH-induced tissue injury. ROS accumulation is triggered by a series of cytokines released in a paracrine, autocrine or endocrine manner from cells exposed to EtOH. In the heart, angiotensin II (Ang II)-induced, Nox-dependent ROS generation contributes substantially to EtOH-mediated cytotoxicity and subsequent dysfunction. In the liver, alcohol-induced endotoxemia promotes the release of inflammatory cytokines and ROS generation through multiple mechanisms.

The dual G protein-dependent and -independent signaling actions of RGS6 afforded the unique opportunity to investigate the role of RGS6 in multiple aspects of alcohol pathology. It was hypothesized that RGS6 promotes alcohol seeking behaviors though its ability to negatively regulate neuronal GPCRs while simultaneously mediating ROS-dependent hepatic and cardiac toxicity. As described herein, mice lacking the RGS6 gene are less susceptible to alcohol dependence and are largely protected from hepatic steatosis and alcoholic cardiomyopathy. This work identifies RGS6 as a novel therapeutic target in the treatment of human alcoholics with the potential to reduce alcohol cravings and protect tissues from alcohol-induced damage.

DETAILED DESCRIPTION

Definitions

An "antagonist" (interchangeably termed "inhibitor") of a polypeptide of interest (e.g., RGS6) is an agent that interferes with activation or function of the polypeptide of interest, e.g., partially or fully blocks, inhibits, or neutralizes a biological activity mediated by the polypeptide of interest. For example, an antagonist of RGS6 refers to a molecule that partially or fully blocks, inhibits, or neutralizes a biological activity mediated by RGS6. Examples of inhibitors include antibodies; ligand antibodies; small molecule antagonists; antisense and inhibitory RNA (e.g., siRNA, shRNA) molecules. In certain embodiments, the inhibitor is an antibody or small molecule that binds to RGS6. In a particular embodiment, an inhibitor has a binding affinity (dissociation constant) to the polypeptide of interest of about 1,000 nM or less. In another embodiment, inhibitor has a binding affinity to the polypeptide of interest of about 100 nM or less. In another embodiment, an inhibitor has a binding affinity to the polypeptide of interest of about 50 nM or less. In a particular embodiment, an inhibitor is covalently bound to the polypeptide of interest. In a particular embodiment, the inhibitor inhibits signaling of the polypeptide of interest with an IC50 of 50,000 nM or less. In a particular embodiment, an inhibitor inhibits signaling of the polypeptide of interest with an IC50 of 1,000 nM or less. In another embodiment, an inhibitor inhibits signaling of the polypeptide of interest with an IC50 of 500 nM or less. In another embodiment, an inhibitor inhibits signaling of the polypeptide of interest with an IC50 of 50 nM or less. In certain embodiments, the antagonist reduces or inhibits, by at least 10%, 20%, 30%, 40%, 50%, 60%, 70%, 80%, 90% or more, the expression level or biological activity of the polypeptide of interest. In some embodiments, the polypeptide of interest is RGS6. The term "polypeptide" as used herein, refers to any native polypeptide of interest from any vertebrate source, including mammals such as primates (e.g., humans) and rodents (e.g., mice and rats), unless otherwise indicated. The term encompasses "full-length," unprocessed polypeptide as well as any form of the polypeptide that results from processing in the cell. The term also encompasses naturally occurring variants of the polypeptide, e.g., splice variants or allelic variants. The term also encompasses any synthetic variant of the polypeptide.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "small molecule" refers to any molecule with a molecular weight of about 2000 daltons or less, in certain embodiments about 500 daltons or less.

In certain embodiments, the small molecule is selected from the following compounds, and salts thereof.

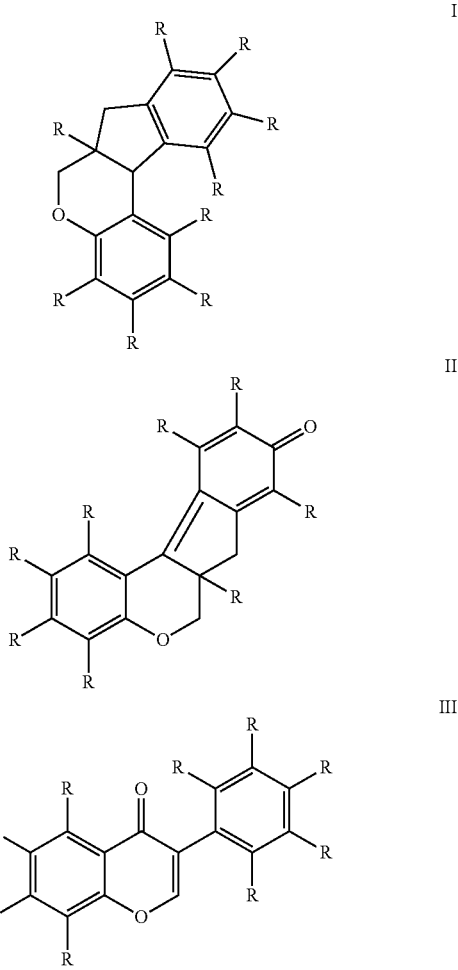

wherein each R is independently H, halogen, OH, (C$_1$-C$_6$)alkyl or O(C$_1$-C$_6$)alkyl, or a salt thereof.

The term "halogen" includes fluoro, chloro, bromo, and iodo.

The term "alkyl" includes a straight chain or branched, noncyclic or cyclic, saturated aliphatic hydrocarbon containing from, e.g., 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

In certain embodiments, the small molecule is selected from the following compounds, and salts thereof. In certain embodiments, the methods exclude the use of any one or combination of the following compounds.

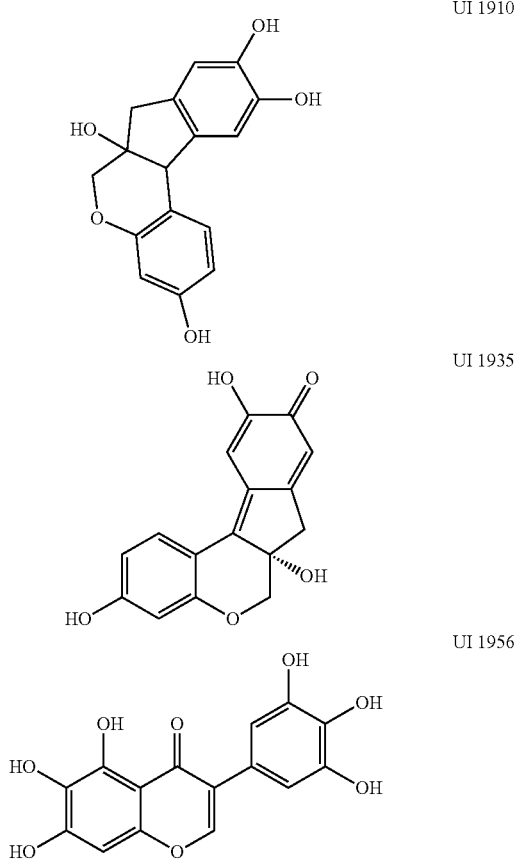

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The terms anti-polypeptide of interest antibody and "an antibody that binds to" a polypeptide of interest refer to an antibody that is capable of binding a polypeptide of interest with sufficient affinity such that the antibody is useful as a diagnostic and/or therapeutic agent in targeting a polypeptide of interest. In one embodiment, the extent of binding of an anti-polypeptide of interest antibody to an unrelated, non-polypeptide of interest protein is less than about 10% of the binding of the antibody to a polypeptide of interest as measured, e.g., by a radioimmunoassay (RIA). In certain embodiments, an antibody that binds to a polypeptide of interest has a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M). In certain embodiments, an anti-polypeptide of interest antibody binds to an epitope of a polypeptide of interest that is conserved among polypeptides of interest from different species. In some embodiments, the polypeptide of interest is RGS6.

A "blocking antibody" or an "antagonist antibody" is one which inhibits or reduces biological activity of the antigen it binds. Preferred blocking antibodies or antagonist antibodies substantially or completely inhibit the biological activity of the antigen.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The terms "full length antibody," "intact antibody," and "whole antibody" are used herein interchangeably to refer to an antibody having a structure substantially similar to a native antibody structure or having heavy chains that contain an Fc region.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

As used herein, the term "targeted therapeutic" refers to a therapeutic agent that binds to polypeptide(s) of interest and inhibits the activity and/or activation of the specific polypeptide(s) of interest. Examples of such agents include antibodies and small molecules that bind to the polypeptide of interest.

An "immunoconjugate" is an antibody conjugated to one or more heterologous molecule(s), including but not limited to a cytotoxic agent.

The term "substantially the same," as used herein, denotes a sufficiently high degree of similarity between two numeric values, such that one of skill in the art would consider the difference between the two values to be of little or no biological and/or statistical significance within the context of the biological characteristic measured by said values (e.g., Kd values or expression). The difference between said two values is, for example, less than about 50%, less than about 40%, less than about 30%, less than about 20%, and/or less than about 10% as a function of the reference/comparator value.

The phrase "substantially different," as used herein, denotes a sufficiently high degree of difference between two numeric values such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

An "effective amount" of a substance/molecule, e.g., pharmaceutical composition, refers to an amount effective, at dosages and for periods of time necessary, to achieve the desired therapeutic or prophylactic result.

A "therapeutically effective amount" of a substance/molecule may vary according to factors such as the disease state, age, sex, and weight of the individual, and the ability of the substance/molecule to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The phrase "pharmaceutically acceptable salt" as used herein, refers to pharmaceutically acceptable organic or inorganic salts of a compound.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human male or female.

The term "concomitantly" is used herein to refer to administration of two or more therapeutic agents, give in close enough temporal proximity where their individual therapeutic effects overlap in time. Accordingly, concurrent administration includes a dosing regimen when the administration of one or more agent(s) continues after discontinuing the administration of one or more other agent(s). In some embodiments, the concomitantly administration is concurrently, sequentially, and/or simultaneously.

By "reduce or inhibit" is meant the ability to cause an overall decrease of 20%, 30%, 40%, 50%, 60%, 70%, 75%, 80%, 85%, 90%, 95%, or greater. Reduce or inhibit can refer to the symptoms of the disorder being treated, the presence or size of metastases, or the size of the primary tumor.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or disorder (e.g., cancer), or a probe for specifically detecting a biomarker described herein. In certain embodiments, the manufacture or kit is promoted, distributed, or sold as a unit for performing the methods described herein.

As is understood by one skilled in the art, reference to "about" a value or parameter herein includes (and describes) embodiments that are directed to that value or parameter per se. For example, description referring to "about X" includes description of "X".

It is understood that aspect and embodiments of the invention described herein include "consisting" and/or "consisting essentially of" aspects and embodiments. As used herein, the singular form "a", "an", and "the" includes plural references unless indicated otherwise.

Antibodies

Provided herein isolated antibodies that bind to a polypeptide of interest, such as RGS6 for use in the methods described herein. In any of the above embodiments, an antibody may be humanized. Further, the antibody according to any of the above embodiments may be a monoclonal antibody, including a chimeric, humanized or human antibody. In one embodiment, the antibody is an antibody fragment, e.g., a Fv, Fab, Fab', scFv, diabody, or F(ab')$_2$ fragment. In another embodiment, the antibody is a full length antibody, e.g., an "intact IgG1" antibody or other antibody class or isotype as defined herein.

Binding Polypeptides

Binding polypeptides are polypeptides that bind a polypeptide of interest, including to RGS6, are also provided for use in the methods described herein. In some embodiments, the binding polypeptides are RGS6 antagonists. Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding, preferably specifically, to a target, e.g., RGS6.

Binding Small Molecules

Provided herein are binding small molecules for use as a binding small molecule antagonist of a polypeptide of interest such as RGS6 for use in the methods described above. In some embodiments, the binding small molecule antagonist inhibits RGS6 activity.

Binding small molecules are in certain embodiments organic molecules other than binding polypeptides or antibodies as defined herein that bind, preferably specifically, to RGS6.

Examples of small molecule antagonists of RGS6 that may be useful in the practice of certain embodiments include those small molecules described herein.

Binding small molecules may be identified and chemically synthesized using known methodology (see, e.g., PCT Publication Nos. WO00/00823 and WO00/39585). Binding small molecules are usually less than about 2000 daltons in size, alternatively less than about 1500, 750, 500, 250 or 200 daltons in size, wherein such small molecules that are capable of binding, preferably specifically, to a polypeptide as described herein may be identified without undue experimentation using well known techniques. In this regard, it is noted that techniques for screening organic small molecule libraries for molecules that are capable of binding to a polypeptide of interest are well known in the art (see, e.g., PCT Publication Nos. WO00/00823 and WO00/39585). Binding organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

Antagonist Polynucleotides

Provided herein are also polynucleotide antagonists for use in the methods described herein. The polynucleotide may be an antisense nucleic acid and/or a ribozyme. The antisense nucleic acids comprise a sequence complementary to at least a portion of an RNA transcript of a gene of interest, such as an RGS6 gene. However, absolute complementarity, although preferred, is not required.

A sequence "complementary to at least a portion of an RNA," referred to herein, means a sequence having sufficient complementarity to be able to hybridize with the RNA, forming a stable duplex; in the case of double stranded antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a RNA it may contain and still form a stable duplex (or triplex as the case may be). One skilled in the art can ascertain a tolerable degree of mismatch by use of standard procedures to determine the melting point of the hybridized complex.

Polynucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, *Nature* 372:333-335. Thus, oligonucleotides complementary to either the 5'- or 3'-non-translated, non-coding regions of the gene, could be used in an antisense approach to inhibit translation of endogenous mRNA. Polynucleotides complementary to the 5' untranslated region of the mRNA should include the complement of the AUG start codon. Antisense polynucleotides complementary to mRNA coding regions are less efficient inhibitors of translation but could be used in accordance with the invention. Whether designed to hybridize to the 5'-, 3'- or coding region of an mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Antibody and Binding Polypeptide Variants

In certain embodiments, amino acid sequence variants of the antibodies and/or the binding polypeptides provided herein are contemplated. For example, it may be desirable to improve the binding affinity and/or other biological properties of the antibody and/or binding polypeptide. Amino acid sequence variants of an antibody and/or binding polypeptides may be prepared by introducing appropriate modifications into the nucleotide sequence encoding the antibody and/or binding polypeptide, or by peptide synthesis. Such modifications include, for example, deletions from, and/or insertions into and/or substitutions of residues within the amino acid sequences of the antibody and/or binding polypeptide. Any combination of deletion, insertion, and substitution can be made to arrive at the final construct, provided that the final construct possesses the desired characteristics, e.g., antigen-binding.

In certain embodiments, antibody variants and/or binding polypeptide variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes Amino acid substitutions may be introduced into an antibody and/or binding polypeptide of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Methods of Screening and/or Identifying Antagonists of RGS6 with Desired Function Additional antagonists of a polypeptide of interest, such as RGS6 for use in the methods described herein, including antibodies, binding polypeptides, and/or small molecules have been described. Additional antagonists of such as anti-RGS6 antibodies, binding polypeptides, and/or binding small molecules provided herein may be identified, screened for, or characterized for their physical/chemical properties and/or biological activities by various assays known in the art. Accordingly, certain embodiments of the invention are directed to screening methods for identifying agents useful for treating the behavioral actions of alcohol and, e.g., hepatic steatosis, cardiomyopathy (including fibrosis) and gastrointestinal damage.

In certain embodiments, a computer system comprising a memory comprising atomic coordinates of RGS6 polypeptide are useful as models for rationally identifying compounds that a ligand binding site of RGS6. Such compounds may be designed either de novo, or by modification of a known compound, for example. In other cases, binding compounds may be identified by testing known compounds to determine if the "dock" with a molecular model of RGS6. Such docking methods are generally well known in the art.

An RGS6 crystal structure data can be used in conjunction with computer-modeling techniques to develop models of binding of various RGS6-binding compounds by analysis of the crystal structure data. The site models characterize the three-dimensional topography of site surface, as well as factors including van der Waals contacts, electrostatic interactions, and hydrogen-bonding opportunities. Computer simulation techniques are then used to map interaction positions for functional groups including but not limited to protons, hydroxyl groups, amine groups, divalent cations, aromatic and aliphatic functional groups, amide groups, alcohol groups, etc. that are designed to interact with the model site. These groups may be designed into a pharmacophore or candidate compound with the expectation that the candidate compound will specifically bind to the site. Pharmacophore design thus involves a consideration of the ability of the candidate compounds falling within the pharmacophore to interact with a site through any or all of the available types of chemical interactions, including hydrogen bonding, van der Waals, electrostatic, and covalent interactions, although in general, pharmacophores interact with a site through non-covalent mechanisms.

The ability of a pharmacophore or candidate compound to bind to RGS6 polypeptide can be analyzed in addition to actual synthesis using computer modeling techniques. Only those candidates that are indicated by computer modeling to bind the target (e.g., RGS6 polypeptide binding site) with sufficient binding energy (in one example, binding energy corresponding to a dissociation constant with the target on the order of $10^{-2}$ M or tighter) may be synthesized and tested for their ability to bind to RGS6 polypeptide and to inhibit RGS6, if applicable, enzymatic function using enzyme assays known to those of skill in the art and/or as described herein. The computational evaluation step thus avoids the unnecessary synthesis of compounds that are unlikely to bind RGS6 polypeptide with adequate affinity.

RGS6 pharmacophore or candidate compound may be computationally evaluated and designed by means of a series of steps in which chemical entities or fragments are screened and selected for their ability to associate with individual binding target sites on RGS6 polypeptide. One skilled in the art may use one of several methods to screen chemical entities or fragments for their ability to associate with RGS6 polypeptide, and more particularly with target sites on RGS6 polypeptide. The process may begin by visual inspection of, for example a target site on a computer screen, based on the RGS6 polypeptide coordinates, or a subset of those coordinates known in the art.

To select for an antagonist which induces cancer cell death, loss of membrane integrity as indicated by, e.g., propidium iodide (PI), trypan blue or 7AAD uptake may be assessed relative to a reference. A PI uptake assay can be performed in the absence of complement and immune effector cells. A tumor cells are incubated with medium alone or medium containing the appropriate combination therapy. The cells are incubated for a 3-day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN® flow cytometer and FACSCONVERT® CellQuest software (Becton Dickinson). Those antagonists that induce statistically significant levels of cell death compared to media alone and/or monotherapy as determined by PI uptake may be selected as cell death-inducing antibodies, binding polypeptides or binding small molecules.

In some embodiments of any of the methods of screening and/or identifying, the candidate antagonist of RGS6 is an antibody, binding polypeptide, binding small molecule, or polynucleotide. In some embodiments, the antagonist of RGS6 is an antibody. In some embodiments, the antagonist of RGS6 is a binding small molecule. In some embodiments, the RGS6 antagonist inhibits RGS6 activity.

Pharmaceutical Formulations

Pharmaceutically acceptable carriers are generally non-toxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antagonist of RGS6 and/or cancer therapy agent (e.g., targeted therapy, chemotherapy, and/or radiotherapy) which matrices are in the form of shaped articles, e.g., films, or microcapsules.

The formulations to be used for in vivo administration are generally sterile. Sterility may be readily accomplished, e.g., by filtration through sterile filtration membranes.

Certain embodiments of the invention will now be illustrated by the following non-limiting Examples.

Example 1

The results depicted herein describe a unique and multifarious role for RGS6 in the pathogenesis of alcoholism and alcohol-induced cardiac, gastrointestinal and hepatic damage. It is believed that RGS6 is the only gene with a demonstrated ability to promote alcohol seeking behaviors while simultaneously exacerbating the pathological impact of alcohol consumption on the heart, stomach, intestine and liver. Thus, any drug designed to inhibit RGS6 function would be expected to reduce alcohol cravings while simultaneously protecting the liver and heart from alcohol-mediated damage. Of particular note, the ability of RGS6 to regulate these processes involves very distinct cellular mechanisms. In the central nervous system, the canonical function of RGS6 as a G protein regulator affords it the capacity to inhibit G protein-coupled $GABA_BR$ signaling and disrupt the expression of genes required for dopamine synthesis, release and reuptake in the mesolimbic system, specifically the VTA. Conversely, in the gastrointestinal epithelium, cardiac myocytes and hepatocytes RGS6 promotes alcohol-induced apoptosis in part via its ability to promote Nox-derived ROS generation. Previous studies have demonstrated that the ability of RGS6 to facilitate ROS generation in response to multiple cytotoxic stimuli is independent of its ability to regulate G proteins (Maity et al., J Biol Chem. 2011; 286(2):1409-19). These dichotomous actions of RGS6 in alcohol pathology highlight its distinctive utility as a potential therapeutic target not only to reduce alcohol cravings in alcoholics, but also to ameliorate the pathologic effects of chronic alcohol consumption in multiple susceptible tissues including the liver and heart.

The results presented herein provide striking new evidence that RGS6 functions as a critical mediator of alcohol seeking behaviors in mice. Genetic ablation of RGS6 resulted in amelioration of alcohol consumption in both acute and chronic EtOH free choice feeding paradigms. In the brain, alcohol produces a comparatively rapid and robust RGS6 up-regulation that appears to be unique to the VTA, a region of the brain heavily implicated in addiction. Elevations in dopamine release from the VTA are known to mediate the initial stages in the acquisition of alcohol dependence. In this brain region, $G\alpha_{i/o}$-coupled GPCRs block vesicular dopamine release and induce surface trafficking of DAT, which reduces synaptic dopamine bioavailability. Thus the ability of RGS6 to promote alcohol seeking behaviors is thought to be due to potentiation of one or more $G\alpha_{i/o}$-coupled receptors in this brain region. Moreover, new evidence is provided that RGS6 modulates expression of multiple genes involved in dopamine synthesis (TH), packaging (VMAT2) and reuptake (DAT) needed for dopamine homeostasis or responses to EtOH in the VTA through a yet-to-be elucidated mechanism.

Consistent with this supposition, mice lacking $G\beta_5$, a protein responsible for stabilizing R7 subfamily RGS6 proteins including RGS6, exhibit a reduction in basal dopamine levels in the dorsal striatum, indicating that RGS protein-$G\beta_5$ complexes are important determinants of dopamine bioavailability (46). Thus the proposed model whereby RGS6 promotes alcohol consumption by terminating $G\alpha_{i/o}$-mediated inhibition of dopamine release downstream of $G\alpha_{i/o}$-coupled GPCRs (e.g. $GABA_BR$) remains one possible mechanism to explain the phenotype of reduced alcohol seeking behavior observed in $RGS6^{-/-}$ mice. Indeed, blockade of $GABA_BRs$ with the central nervous system-permeable antagonist SCH-50911 partially reversed the reduction in acute EtOH consumption observed in $RGS6^{-/-}$ mice, which implicates inhibition of $GABA_BR$ signaling in RGS6-mediated alcohol dependence.

The lack of complete phenotype reversal with SCH-50911 could be due either to an insufficient dose of drug or the involvement of additional receptor signaling cascades in RGS6-dependent alcohol consumption. Because RGS6 modulates multiple EtOH-dependent behaviors including consumption, reward and drug withdrawal, RGS6 actions in other brain regions may also contribute to alcohol-dependent behaviors modified by RGS6. Of note, $5-HT_{1A}Rs$ have been shown to ameliorate alcohol withdrawal likely due to actions at post-synaptic sites. Similarly, MORs promote diverse alcohol-related behaviors including consumption and reward, but not withdrawal by modulating dopamine release in the mesolimbic circuit. The increase in GPCR-mediated cortical MAPK activation in $RGS6^{-/-}$ mice is also intriguing given the observed reduction in MAPK phosphorylation in the cortex of opiate addicts.

Acute EtOH intoxication is associated with sedation, mild cognitive impairment and ataxia at lower blood alcohol concentrations. Interestingly, while RGS6 deficiency reduced alcohol reward, consumption and withdrawal it failed to impact the effect of alcohol on motor coordination or consciousness. These results imply that inhibition of RGS6 represents a viable means to reduce alcohol cravings and withdrawal without potentiating the sedative and ataxic effects of EtOH should a patient relapse. This behavioral selectivity represents an advantage over therapeutics such as baclofen, which possesses its own potent sedative and ataxic actions.

Studies in rodents have identified the Ang II-$AT_1R$-Nox axis as a critical determinant of the apoptotic and fibrotic response to long-term EtOH exposure in heart. Ang II has also been implicated in human alcoholic cardiomyopathy as susceptibility to this disease is associated with polymorphisms in the angiotensin-converting enzyme gene (ACE) and levels of circulating Ang II are elevated in alcohol abusers. As described herein, $RGS6^{-/-}$ mice are protected against alcoholic cardiomyopathy including heart hypertrophy, fibrosis, microfilament disarray, and apoptosis. RGS6 mediates Nox-derived ROS generation and Nox-dependent apoptosis in alcohol-treated VCM. Hypertrophic and pro-fibrotic factors are released from dying and damaged myocytes to promote repair, maintain the functional integrity of the heart, and ensure proper cardiac output. Because VCM in the myocardium of $RGS6^{-/-}$ mice fail to undergo apoptosis to the extent observed in WT tissue, the lack of heart hypertrophy and amelioration of fibrosis likely result from a lack of alcohol-induced VCM toxicity. Thus, RGS6, transiently induced by EtOH, is a crucial upstream critical factor required for Nox-mediated cardiac dysfunction following chronic alcohol exposure.

The accumulation of ROS in hepatocytes is one proposed mechanism leading to hepatic dysfunction in alcoholics. Nox complexes, activated by diverse stimuli including Ang II, $TNF\alpha$, and endotoxin, appear to represent the source of EtOH-induced ROS as it has long been known that mice lacking the p47phox subunit of Nox1/2 are protected from alcoholic liver disease. Similar to results obtained in isolated VCM, $RGS6^{-/-}$ hepatocytes were also protected against alcohol-induced ROS accumulation and cell death. In vivo, livers isolated from RGS6 deficient animals following chronic alcohol treatment exhibited a dramatic reduction in apoptosis as well as macrovesicular hepatic steatosis. Unsurprisingly, plasma ALT and triglycerides were consistently lower in $RGS6^{-/-}$ mice treated with alcohol compared to their WT counterparts. Though ROS accumulation can influence fatty acid metabolism in the liver, RGS6 also appears to influence a number of genes involved in fatty acid synthesis including PPARG, FASN, and ACACA through a yet-to-be-elucidated mechanism. Nevertheless, alcohol-induced up-regulation of RGS6 in the liver clearly plays a critical role in mediating both the cell death and accumulation of fatty acids in the liver of alcohol-treated mice, steps known to precede the development of liver cirrhosis in human patients.

While the hepatocyte- and VCM-intrinsic mechanisms described above likely contribute substantially to the protective effect of RGS6 deficiency on alcoholic cardiomyopathy and hepatic steatosis, further experiments revealed an additional endocrine mechanism that likely also plays a role in this process. Emerging evidence suggests that acute ethanol exposure causes damage to the gastrointestinal lining leading to an increase in the permeability of the gut mucosa to intragastric macromolecules including bacterial derived endotoxin. The resultant endotoxemia triggers the release of ROS and pro-inflammatory cytokines in both liver and heart, which act in an autocrine, paracrine, and endocrine manner to exacerbate tissue damage. As described herein, RGS6 is expressed in the epithelium of the stomach and small and large intestines. Further, the gastrointestinal epithelium of mice lacking RGS6 exhibited a dramatic reduction in EtOH-induced apoptotic cell death. Due to maintenance of the gastrointestinal mucosa, the leakage of endotoxin into the circulation was also reduced in $RGS6^{-/-}$ mice. In addition, levels of the pro-inflammatory cytokine $TNF\alpha$ were lower in $RGS6^{-/-}$ mice exposed to alcohol compared to their WT counterparts. Thus, it is likely that the lack of intestinal barrier dysfunction observed in alcohol treated $RGS6^{-/-}$ mice also serves to protect the heart and liver from further damage.

Few therapeutics have proven effective in treating alcoholism in human patients. Currently, acamprosate is first-line pharmacotherapy aimed at reducing cravings and withdrawal in alcoholics. Though generally well tolerated, acamprosate is most effective when combined with psychotherapy and abstinence from alcohol. Similarly, the opioid antagonist naltrexone is approved for use in human alcoholics, but is generally only effective in combination with supportive therapy and in a subset of patients harboring a single nucleotide polymorphism in the MOR gene rendering them more susceptible to alcohol addiction and relapse. There are currently no drugs marketed for the express purpose of reducing alcohol-mediated damage in the heart and liver. Given the prevalence of alcohol abuse worldwide, there is a clear need for more effective therapeutics. As described herein, it has been discovered that RGS6 inhibition represents a novel means to counteract alcohol dependence by opposing alcohol-induced dopamine release via potentiation $G\alpha_i$-coupled GPCRs in the VTA. At the same time, loss of RGS6 function ameliorates the cytotoxic actions of alcohol in the heart and liver through simultaneous reduction of alcohol-induced, ROS-mediated pro-apoptotic signaling in hepatocytes and VCM and prevention of gastrointestinal barrier dysfunction.

Results

RGS6 Loss Ameliorates Alcohol Seeking, Conditioned Reward and Withdrawal in Mice without Impacting EtOH-Induced Sedation and Ataxia To evaluate the impact of RGS6 loss on alcohol consumption, wild type (WT) and RGS6$^{-/-}$ mice were provided free access to two bottles of drinking water with and without EtOH (8%). Remarkably, mice lacking RGS6 consume significantly less EtOH and exhibit a reduction in EtOH preference in this short-term free choice paradigm. No differences were observed in water consumption or forced EtOH consumption. Mice of both genotypes were also subjected to a long-term model of binge drinking in which they were provided free access to water with and without EtOH. The concentration of EtOH in the water increased weekly from 3% to 20% for a total period of one month. RGS6$^{-/-}$ mice were significantly less susceptible to alcohol seeking behaviors compared to WT mice in this test. Because ethanol produces taste responses (sweet and bitter), it is necessary to confirm whether changes in EtOH consumption are secondary to changes in taste preference in genetically modified mice. To rule out effects of RGS6 on taste preference, mice were also tested for their consumption of sweet (saccharin) and bitter (quinine) solutions. Results revealed no effect of genotype on bitter or sweet taste preference, respectively. These results demonstrate that RGS6 loss results in a reduction in alcohol seeking behaviors in mice.

Voluntary EtOH consumption and preference are known to correlate well with measures of EtOH reward. Consistent with the observed reduction in alcohol drinking, RGS6$^{-/-}$ mice were less susceptible to EtOH-mediated conditioned reward. Further, mice lacking RGS6 experienced less severe withdrawal symptomology and recovered faster from EtOH withdrawal compared to their WT counterparts. In contrast, no differences were observed in EtOH-induced sedation, and, while RGS6$^{-/-}$ mice exhibit a baseline ataxic phenotype as we previously reported (21), the net effect of EtOH on motor coordination was equivalent or reduced in mice lacking RGS6 compared to WT mice.

RGS6-Mediated Regulation of GABA$_B$R Signaling Contributes to Alcohol Seeking Behaviors in Mice RGS6 was identified as a critical negative regulator of cerebellum GABA$_B$R-regulated motor behavior (Maity et al., J Biol Chem. 2012; 287(7):4972-81). The involvement of GABA$_B$R signaling in the reduction in alcohol drinking observed in mice lacking RGS6 was investigated. Though no difference in EtOH-induced sedation was observed in RGS6$^{-/-}$ mice, RGS6 mice are remarkably sensitized to the sedative effects of baclofen. These results indicate that EtOH and baclofen control consciousness through distinct pathways, likely explaining the reported additive hypnotic effects of EtOH and baclofen. Both the time course of GABA$_B$R-induced activation and deactivation of the mitogen activated protein kinase (MAPK) signaling cascade were pro-longed in the cortex of RGS6$^{-/-}$ mice. These data indicate that RGS6 is also capable of regulating non-cerebellar populations of GABA$_B$Rs. To directly test the involvement of GABA$_B$R signaling in the reduction in alcohol seeking behavior seen in RGS6$^{-/-}$ mice, the short-term free choice EtOH consumption paradigm was repeated with the addition of daily GABA$_B$R antagonist treatments. Treatment with SCH-50911 partially reversed the reduction in alcohol consumption observed in RGS6$^{-/-}$ mice indicating that potentiation of GABA$_B$R signaling underlies, in part, the reduction in voluntary alcohol consumption observed in mice lacking RGS6.

RGS6 is Up-Regulated by EtOH in the VTA where it Regulates Genes Controlling Dopamine Bioavailability RGS6 expression in dopaminergic neurons of the VTA was investigated. IHC staining revealed robust RGS6 expression in the VTA of WT mice that was lost in RGS6$^{-/-}$ animals. Co-staining with the dopaminergic neuron marker tyrosine hydroxylase (TH) indicated that RGS6 is prominently expressed in a subset of dopamine producing neurons in the VTA. Levels of RGS9, an RGS protein closely related to RGS6, increase in brain reward regions in response to opioids and amphetamines, diminishing their rewarding properties. A robust increase in RGS6 expression was observed in the VTA of mice given free access to increasing concentrations of EtOH with time. The VTA, like cerebellum, expresses multiple RGS6 splice forms. G$\beta_5$, an RGS6 binding partner required for RGS6 stability, followed an identical trend though the fold induction was lower in magnitude. No dramatic alterations in RGS6/G$\beta_5$ expression were observed in the cerebellum. However, EtOH did induce a reduction in RGS6 expression after approximately 4 weeks of exposure in the cortex and striatum. In addition, changes in RGS6 expression appear to require prolonged EtOH exposure as a single dose of EtOH was insufficient to cause alterations in RGS6 expression in any tissue surveyed. In addition, no changes in G$\beta_5$ expression were detected following a single EtOH dose or prolonged exposure in non-VTA brain regions. However, the closely related RGS protein RGS7, a fellow member of the R7 family of RGS proteins, was also up-regulated in the VTA indicating it too may participate in alcohol reward.

Activation of G$\alpha_{i/o}$ in dopaminergic neurons blocks dopamine release and up-regulates the dopamine transporter (DAT) both of which reduce synaptic dopamine bioavailability required for alcohol reward. The mRNA expression of the dopamine synthesizing enzyme (TH) and the enzyme responsible for transporting dopamine into vesicles for synaptic release, vesicular monoamine transporter 2 (VMAT2) were reduced in RGS6$^{-/-}$ mice. Interestingly, though no difference was observed under control conditions, a dramatic increase in DAT expression was observed specifically in the VTA of RGS6$^{-/-}$ mice following chronic EtOH exposure. The dependence of this phenomenon on EtOH appears to be unique to the VTA as expression of DAT was increased under control conditions in the striatum. Unlike the trend observed in the VTA, TH expression is higher in the striatum of RGS6$^{-/-}$ mice and no changes were observed in VMAT2 levels. These results indicate that, in WT mice, RGS6 inhibits an EtOH-induced mechanism (possibly GPCR-G$\alpha_{i/o}$-mediated) that promotes DAT up-regulation in the VTA. Up-regulation of DAT in response to EtOH, as well as reduced expression of TH and VMAT2 under control conditions, would be expected to limit dopamine bioavailability required to promote EtOH reward and may contribute to the reduction in alcohol seeking behaviors and conditioned reward observed in mice lacking RGS6.

Mice Lacking RGS6 are Protected Against Alcohol-Induced Cardiomyopathy

Having established a critical role for RGS6 in promoting alcohol seeking behaviors, the involvement of RGS6 in the pathogenesis of cardiac damage induced by EtOH was investigated. A chronic feeding protocol was used in which WT and RGS6$^{-/-}$ mice were allowed free access to a Lieber-DeCarli control or isocaloric 5% EtOH containing liquid diet for 2 months. This "forced" EtOH feeding paradigm, which eliminates genotype effects on EtOH seeking and reward behaviors, has been shown to cause detectable loss of cardiac function in addition to compromising liver function. During the course of treatment both WT and RGS6$^{-/-}$ mice lost weight. However, though the weight loss was accelerated in mice lacking RGS6, they consistently drank more of the alcohol-containing food compared to their WT counterparts with their consumption more closely resembling that of mice consuming the control diet indicating the daily dose of EtOH was higher for RGS6$^{-/-}$ mice and highlighting the lack of alcohol taste aversion in RGS6$^{-/-}$ mice.

Cardiotoxic stimuli can induce up-regulation of RGS6 in heart (Yang et al., Cancer Res. 2013; 73(6):1662-7). Despite the lack of a detectable increase in RGS6 expression at the end of the 2 month treatment protocol (data not shown), a transient rise in RGS6 protein levels was observed in heart after 2 weeks of ethanol exposure that returned to baseline by 1 month. Consistent with previous reports, chronic EtOH treatment resulted in cardiac hypertrophy, fibrosis, and myofilament disarray. However, mice lacking RGS6 were significantly protected from these pathogenic aberrations despite the observation that they in fact consumed more of the EtOH-containing diet. Importantly, the differences in the cytotoxic actions of RGS6 in the heart were not due to differential EtOH absorption and/or metabolism as blood alcohol concentration following oral EtOH administration was equivalent in WT and RGS6$^{-/-}$ mice. These results provided intriguing new evidence implicating RGS6 as a critical component of the signaling cascade(s) contributing to alcoholic cardiomyopathy.

RGS6 Promotes Apoptosis in Alcohol Treated Ventricular Cardiac Myocytes (VCM) Via a Nox-Dependent Mechanism Alcohol induces apoptosis in isolated VCM by triggering Ang II-induced, Nox-dependent ROS generation. A striking reduction in apoptotic nuclei was observed in the myocardium of mice lacking RGS6. In keeping with the requirement for ROS generation in the cytotoxic actions of alcohol, EtOH-induced ROS production was reduced in cells lacking RGS6. To determine the enzymatic source of RGS6-dependent ROS production, VCM were treated with the Nox complex inhibitor diphenyleneiodonium (DPI). Indeed, Nox-dependent ROS generation in response to alcohol was completely RGS6-dependent as DPI significantly reduced ROS generation in WT but not RGS6$^{-/-}$ VCM. The alcohol-induced apoptotic response was also dependent on Nox-mediated ROS generation in WT, but not RGS6$^{-/-}$ VCM. These results provide the first evidence that RGS6 has a critical role as an upstream activator of Nox-derived ROS required for alcohol-induced VCM apoptosis. The lack of Nox-dependent ROS generation and apoptosis in VCM likely contributes to the amelioration of alcohol-induced cardiac apoptosis, fibrosis and hypertrophy observed in mice lacking RGS6.

RGS6 Deficiency Ameliorates Alcoholic Hepatic Steatosis and Apoptosis

The most common long-term health complication associated with chronic alcohol abuse is hepatic cirrhosis, a disease that begins with extensive fatty acid deposition in the liver. Two months of alcohol exposure is sufficient to initiate this process in mice. Like alcoholic cardiomyopathy, removal of Nox-derived ROS ameliorates alcoholic hepatic steatosis. Very little RGS6 is detectable in the liver under basal conditions, but 2 weeks of chronic alcohol consumption is sufficient to up-regulate RGS6 by several fold. Strikingly, mice lacking RGS6 were substantially protected against alcohol-induced liver hypertrophy, fatty acid accumulation, and macrovesicular hepatic steatosis. Liver function test revealed a modest alcohol-dependent increase in plasma aspartate transaminase (AST), alanine transaminase (ALT) and triglycerides. While mice lacking RGS6 exhibited a similar increase in AST compared to their WT counterparts, RGS6$^{-/-}$ mice were protected against alcohol-induced increases in circulating ALT and triglyceride levels. To provide some mechanistic insight into the role of RGS6 in fatty acid metabolism in the liver, the cellular content of various genes involved in fatty acid synthesis and oxidation were measured in the liver. mRNA levels of the nuclear receptors peroxisome proliferator-activated receptors a (PPARa) and γ (PPARy) were lower in the livers of RGS6$^{-/-}$ mice irrespective of ethanol treatment. As PPARy is involved in fatty acid synthesis, this reduction would be expected to protect mice against pathological fatty acid accumulation. Similarly, while expression of fatty acid synthase (FASN) was increased in the livers of alcohol-treated WT mice, no such increase was observed in RGS6$^{-/-}$ mice, which also exhibit a baseline reduction in FASN and acetyl-CoA carboxylase (ACACA). Together, these data indicate that RGS6 modulates baseline expression of multiple genes impinging upon fatty acid homeostasis in the liver, the reduction of which likely protects against liver disease.

Whether RGS6 deficiency protects against hepatic ROS generation and apoptosis was also investigated in alcohol treated cells via a hepatocyte-intrinsic mechanism. Similar to results observed in heart, the number of apoptotic cells in the liver of RGS6$^{-/-}$ mice was dramatically reduced. Interestingly, in vivo, alcohol exposure triggered up-regulation of RGS6 in isolated hepatocytes. Further, similar to trends we observed in isolated VCM, the ability of alcohol to trigger increases in ROS levels and cellular apoptosis in hepatocytes was compromised in cells lacking RGS6. These results indicate that RGS6 protects hepatocytes from alcohol-induced damage via, at least in part, hepatic parenchymal actions of RGS6 in pro-apoptotic signaling cascades.

RGS6$^{-/-}$ Mice Exhibit a Reduction in Alcohol-Induced Gastrointestinal Apoptosis and Endotoxemia While the aberrations in gene expression and a loss of alcohol-induced, pro-apoptotic ROS generation in VCM and hepatocytes likely contributes substantially to the protective effect of RGS6 loss on alcoholic cardiomyopathy and hepatic steatosis, further experiments revealed an additional endocrine mechanism that likely also plays a role in these processes. Recent evidence suggests that acute ethanol exposure causes damage to the gastrointestinal mucosa leading to an increase in the permeability of the gut mucosa to intragastric macromolecules such as bacterial derived endotoxin. The resultant endotoxemia triggers the release of ROS and pro-inflammatory cytokines (e.g., tumor necrosis factor α, TNFα), which act in an autocrine, paracrine, and endocrine manner to cause tissue damage. It has been discovered that RGS6 is expressed in appreciable levels in the epithelium of the stomach and small and large intestines. Based on this observation, the impact of RGS6 loss on alcohol-induced gastric barrier dysfunction was investigated.

Because a robust increase in gastrointestinal epithelium apoptosis and leakage of endotoxin into the blood is detectable rapidly after alcohol exposure, an acute three dose alcohol treatment regimen was used for these studies. No up-regulation of RGS6 was observed in the gut following this short treatment regimen, and histological analysis revealed similar intestinal crypt architecture in mice of both genotypes. However, while large clusters of apoptotic cells were evident in intestinal sections from WT mice, more diffuse apoptosis was seen in the intestinal epithelium of RGS6$^{-/-}$ mice. Mice lacking RGS6 were also protected from alcohol-induced gastric hemorrhage. Consistent with the histopathological analyses, levels of serum endotoxin were significantly lower in RGS6$^{-/-}$ mice. Further, while a difference in serum and stomach TNFα levels in mice of the two genotypes was not detected, TNFα content was lower in the intestine, liver, and heart of RGS6$^{-/-}$ mice exposed to alcohol compared to their WT counterparts. Taken together, these results demonstrate that RGS6 deficiency allows for maintenance of the intestinal barrier, prevents leakage of endotoxin into the circulation and reduces endotoxin-stimulated release of pro-inflammatory cytokines in multiple susceptible tissues.

Materials and Methods

Mice

RGS6$^{-/-}$ mice were generated as described recently (Yang et al., Circ Res. 2010; 107(11):1345-9). Experiments were performed using age-matched (10-12 weeks) WT and RGS6$^{-/-}$ litter mates. Mice were housed on a 12 h light/dark cycle and behavioral experiments performed during the light cycle. Animals of both genders were used for experiments as no gender-specific differences were observed in mouse performance. Animals naïve to each paradigm were used for all behavioral experiments. Drugs were administered 30 min prior to behavioral testing via intraperitoneal (i.p.) injection unless otherwise noted. For all animal experiments, analyses were performed by an observer blinded to mouse genotype and drug treatment. Experiments were performed in agreement with the Guide for the Use and Care of Laboratory Animals.

Short-Term Alcohol Consumption

Short-term alcohol consumption was measured in WT and RGS6$^{-/-}$ mice essentially as previously described (Lockridge et al., Alcohol. 2012; 46(4):389-400). First, mice were individually housed for 2 days prior to the experiment. Each cage was then outfitted with two drinking bottles made from graduated serological pipettes sealed with parafilm to prevent evaporation and attached to each cage. Both bottles were initially filled with tap water for three days, then one each with water or a solution containing 8% EtOH, and finally 8% EtOH in both bottles for two more days. The position of the bottles was alternated to avoid place preference bias. Volume levels were recorded daily, tubes refilled and mice weighed. Alcohol consumption by volume or weight was reported normalized to individual mouse body weight. In a follow-up experiment, mice received i.p. injections (12.5 mg/kg) of SCH-50911, the GABA$_B$R antagonist, daily on days when given access (either free or forced) to alcohol. One week after completion of the alcohol drinking procedure, taste preference was examined by measuring saccharin (sweet, no caloric value) fluid intake by presenting 0.04% followed by 0.08% saccharin solutions and quinine (bitter, no caloric value) fluid intake by presenting 20 mM and 40 mM quinine containing solutions for 1 week each. Alcohol (or saccharin/quinine) preference was calculated by dividing the EtOH volume consumed by the total fluid intake.

Two Bottle Choice Test

Alcohol consumption and preference were assessed in mice using the two bottle choice test, a model of binge alcohol consumption, essentially as previously described (Bahi, Neuroscience. 2011; 199(13-23). Mice were individually housed and given 24 h access to both bottles, one containing standard tap water and the other containing an alcohol solution increasing in concentration every week from 3% to 6%, 10% and finally 20% alcohol by volume. EtOH consumption was measured each week along with animal weight. Bottle positions were changed periodically to avoid side preference. For the alcohol drinking experiment average alcohol consumption per day was calculated and normalized to body weight.

Acute Withdrawal Severity

EtOH withdrawal-induced seizure activity was evaluated by scoring handling-induced convulsions (HIC) essentially as previously described (Bahi, Neuroscience. 2011; 199(13-23). HIC scoring was performed hourly for 12 hours following a single EtOH dose (4 g/kg i.p.). Each mouse was picked up by the tail and behavior observed. The scoring scale ranged from a score of 0 (no convulsion) to 7 (full tonic-clonic convulsion). As previously reported, scores rarely exceeded a value of 4. Both the hourly HIC scores and area under the curve (AUC) calculated using Graphpad Prism Software are reported.

Conditioned Place Preference

Prior to conditioning mice were habituated to the testing apparatus. During this phase, mice were placed in the center of the chamber after a saline injection (10 ml/kg, i.p.) and allowed to freely explore for 15 minutes. The conditioning phase involved a series of twelve, 5 minute sessions in which saline or ethanol (2 g/kg, i.p.) doses were administered and the mouse restricted to the associated side of the chamber (ethanol: white walls, textured floor; saline: dark walls, smooth floor). Each animal received six conditioning trials with each treatment/chamber pairing. Following the conditioning phase, animals were again given a single saline injection and allowed free access to both compartments after placement in the center of the cage. The amount of time spent in each chamber during this testing phase was recorded during a 15 minute trial.

Loss of Righting Reflex (LORR)

Mice were given a sedative dose of ethanol (3.2 g/kg i.p.) and placed in a supine position in a V-shaped trough. LORR was defined as the total sleep time and the time required for recovery (re-acquisition of the mouse's ability to right itself 3 times in a 30 second period after placement on its back).

Rotarod Performance Test

WT and RGS6$^{-/-}$ mice were tested on a motorized rotarod apparatus (Columbus Instruments; Columbus, Ohio, USA). Mice were placed on the roller, and the time they remained on it during rotation was measured. Tests were performed at fixed speeds of 5, 10 or 15 rpm and with acceleration (3 rpm/s) from 5 rpm. A maximum of 120 seconds was allowed per mouse for fixed speed tests. One cohort of mice was given a single dose of EtOH (1.75 g/kg, i.p.) 30 min prior to testing.

Balance Beam Test

The balance beam consisted of a plastic cylinder (50 cm long with a diameter of 1 cm) elevated 25 cm above the floor. Mice were trained to run the length of the bream twice prior to testing. As expected based on the known ataxic phenotype of RGS6$^{-/-}$ mice, these animals struggled to complete the training. On the third beam cross the number of footslips and falls and total time required to traverse the beam were recorded by an observed blinded to genotype. If an animal stopped on the beam, its tail was gently pressed to encourage movement and, in the event an animal fell from the beam, it was replaced on the beam at the location from which it fell and allowed to finish the test. One cohort of mice was given a single dose of EtOH (1.75 g/kg, i.p.) 30 min prior to testing.

Immunohistochemistry (IHC)

Formaldehyde (4%)-perfused frozen brain sections from WT and RGS6$^{-/-}$ mice were processed to examine protein expression and localization. Briefly, cryo sections were washed in phosphate-buffered saline (PBS), blocked with 5% BSA and incubated overnight at 4° C. with and without (control) anti-RGS6 rabbit polyclonal antibody or other antibodies where indicated. Following washing four times in PBS (10 min each), sections were incubated for 1 h at room temperature with Alexa Fluor® secondary antibodies (Life Technologies; Carlsbad, Calif., USA). Sections were visualized using confocal microscopy (Zeiss LSM710).

Formalin-fixed, paraffin-embedded sections of gastrointestinal tissue from WT and RGS6$^{-/-}$ mice were obtained from University of Iowa Central Microscopy Facility and were processed to examine expression of different key signaling proteins as we previously described (Maity et al., J Biol Chem. 2011; 286(2):1409-19). Briefly, sections were de-waxed in xylene, treated with a graded series of alcohol solutions, immersed in 3% hydrogen peroxide to block endogenous peroxide activity, blocked with 5% BSA and then incubated overnight at 4° C. with specific antibody. Following washing (3×10 min) in PBS, sections were incubated for 1 h at room temperature with peroxidase-conjugated secondary antibodies. The sections were counterstained in Harris hematoxylin and observed under the microscope.

Immunoblotting

Tissues were rapidly dissected from WT and RGS6$^{-/-}$ mice and flash frozen in liquid nitrogen. Tissue homogenates and cell lysates were prepared in RIPA buffer containing protease (p8340) and phosphatase (#3) inhibitor cocktails (Sigma), quantified and probed. Twenty μg of protein per sample was subjected to SDS-PAGE and immunoblotting using standard techniques. Immunoblots were visualized using the Odyssey Imaging System with appropriate fluorescently labeled secondary antibodies (LI-COR Biosciences; Lincoln, Nebr., USA). Densitometric quantification of western blots was performed utilizing Image J software (NIH). Protein expression was normalized to loading controls and expressed relative to control conditions.

Real Time PCR (RT-PCR)

Tissue mRNA was extracted using the Qiagen RNeasy Mini kit and first stand cDNA synthesis was performed with SuperScript III (Life Technologies). Real time PCR was carried out using iQ™ SYBR® Green Supermix (Bio-Rad; Hercules, Calif., USA) according to the manufacturer's protocol. GAPDH was used as an internal control to normalize RNA levels.

Activity Measurement in Home Cage

The activity of WT and RGS6$^{-/-}$ mice was observed in the home cage following administration of a single dose of baclofen (10 mg/kg, i.p.). After drug treatment mice were placed back in their home cage and behavior videotaped for 20 min. Videos were scored for total immobility time (no discernable ambulation, grooming, social or other behaviors) by an observer blinded to mouse genotype. Data are presented as percent total time spent immobile.

Chronic EtOH Treatment

To assess the impact of RGS6 loss on EtOH-induced hepatic and cardiac toxicity WT (n=8-10) and RGS6$^{-/-}$ (n=8-10) mice were fed on a Lieber-DeCarli control or isocaloric 5% EtOH containing liquid diet (Bio-Serv, Frenchtown, N.J., USA) for 2 months. During the treatment period body weight changes and total EtOH consumption were recorded every 3 days. At the end of the experiment serum was collected to measure plasma ALT, AST, and triglycerides (University of Iowa Hospitals). Liver and heart tissues were weighed and divided for immunoblotting, RT-PCR, and histological analyses. Tissue sections were processed for hematoxylin and eosin (H & E), Oil Red 0 (liver), Masson trichrome (heart) and terminal deoxynucleotidyl transferase dUTP nick end labeling (TUNEL) staining at the University of Iowa Central Microscopy core to detect general histology, liver lipid accumulation, cardiac fibrosis, and apoptotic cells, respectively.

Blood Alcohol Concentration

Mice were injected with EtOH (3.5 g/kg) by oral gavage and blood collected 45 minutes post-injection. Blood samples were transferred to cold EDTA tubes and centrifuged at 2000×g for 10 minutes. Plasma samples were stored at −80° C. until blood alcohol concentrations could be determined at the University of Iowa Hospitals.

Ventricular Cardiomyocyte Isolation and Culture

Primary neonatal VCM were isolated from 2-3 day old WT and RGS6$^{-/-}$ mice according to our previously published protocol (Yang et al., Cancer Res. 2013; 73(6):1662-7). Twenty-four hours after isolation and plating, cells were treated with 200 mM EtOH (24 hours) in the presence or absence of DPI (1 μM, 1.5 hour pre-treatment) where indicated. Apoptosis was measured from cell lysates using the Cell Death Detection ELISA kit (Roche; San Francisco, Calif., USA). This kit quantifies formation of cytoplasmic histone-associated DNA fragments (mono- and oligosomes) originating from apoptotic cell death. Results are expressed as a fold increase in enrichment factor (cytoplasmic nucleosomes). Intracellular ROS generation was estimated using the cell-permeable oxidation-sensitive probe, CM-H$_2$DCFDA (Sigma) as described previously (Maity et al., J Biol Chem. 2011; 286(2):1409-19). Briefly, cells were harvested by centrifugation, washed three times with ice-cold PBS, re-suspended in PBS and incubated with 5 μM CM-H$_2$DCFDA for 20 minutes at 37° C. After incubation cells were again washed and lysed in PBS with 1% Tween 20. ROS level was determined at the ratio of dichlorofluorescein excitation at 480 nm to emission at 530 nm.

Hepatocyte Isolation

Primary adult hepatocytes were isolated from 2 month old WT and RGS6$^{-/-}$ mice according to a standard collagenase perfusion protocol. Cells were suspended in Krebs-Henseleit bicarbonate buffer following isolation and maintained at 37° C. in a humidified cell culture incubator (5% CO$_2$). Cells were treated with EtOH (200 mM) for 2 hours. ROS accumulation and apoptosis were measured as described above.

Gastrointestinal Toxicity

The impact of RGS6 loss on EtOH-induced gastrointestinal dysfunction was evaluated following an acute treatment protocol as previously described (Abdelmegeed et al., Free Radic Biol Med. 2013; 65(1238-45). Briefly, age-matched WT and RGS6$^{-/-}$ mice were exposed to three doses of EtOH (6 g/kg, oral gavage) or dextrose (control) at 12 hour intervals. One hour following the final EtOH dose, blood, intestine, and stomach were harvested for histological (H & E) and biochemical analyses. Serum endotoxin levels were measured using the ToxinSensor™ Chromogenic LAL Endotoxin Assay Kit (GenScript; Piscataway, N.J., USA) according to the manufacturer's instructions. Serum and tissue TNFα levels were detected with the Mouse TNFα ELISA Ready-SET-Go!® (eBioscience; San Diego, Calif., USA) following the manufacturer's protocol.

Statistical Analyses

Data were analyzed by student's t-test or two-way ANOVA with the Bonferroni post hoc adjustment as appropriate. Statistical analyses were performed using Prism software (GraphPad Software; La Jolla, Calif., USA). Results were considered significantly different at p<0.05. Values are expressed as means±S.E.M.

Example 2 Validating RGS6 as a Novel Target for Alcohol Abuse Treatment

No effective drugs are available to treat alcoholism. The discoveries described herein led to the use of high throughput screening (HTS) to identify small molecule inhibitors of RGS proteins (Roman et al. J Med Chem 54: 7433-7440, 2011; Roman et al. Mol Pharmacol 78: 360-365, 2010). Results demonstrating the ability to identify small molecule inhibitors of the GAP activity of RGS6 are provided using a highly sensitive HTS.

Given the discovery that RGS6 promotes the acquisition of alcohol dependence by modulation of one or more GPCR signaling cascades, molecules that inhibit the GAP activity of RGS6 would be expected to attenuate alcohol seeking behavior as observed in mice lacking RGS6.

A high throughput screen based upon the protein-protein interaction between RGS6 and its cognate G protein has been developed. This is an approach used for other RGS proteins (Bodle et al. Future Med Chem 5: 995-1007, 2013; Mackie et al. J Biomol Screen 16: 869-877, 2011; Monroy et al. PloS one 8: e62247, 2013). Briefly, human RGS6 and G protein from E. coli is expressed and purified, which are then chemically modified to attach to microspheres. These microspheres (AlphaScreen) are then dispensed into high density experimental plates, with either 384 or 1536 wells per plate. Into each of these wells, an individual compound is dispensed, and through the use of a chemiluminescent reaction between the RGS6 and G protein coated beads, whether or not the two proteins are interacting is determined. This loss of this chemiluminescent signal indicates that a compound interferes with the proteins interacting with each other, and is a potential "hit" as an inhibitor. A critical measure is the "Z-factor," which indicates the ability to detect an inhibitor based on the screening signal strength, and the difference between positive and negative control values. A Z-factor between 0.5 and 1 is considered to be acceptable, and the Z-factor for the RGS6 assay is quite good, at 0.61. Using this method, a screen of 2320 compounds has been completed in 384-well plates. This screen resulted in the identification of compounds that may inhibit the RGS6-G protein interaction, however at low potency. These compounds are being evaluated in testing for specificity and effectiveness in functional assays. Accessing the much larger 50,000 compound Chembridge library held by UI HTS will allow much larger coverage of "chemical space" to sample chemotypes that may represent RGS6 inhibitors with drug like properties.

Using the AlphaScreen method, the HTS assay will be optimized for use in 1536-well plates. This higher density is needed in order to efficiently screen the larger 50,000 compound library contained in the UI HTS facility. The design of the assay will be adopted from previously published work on RGS proteins. Once compounds are identified from the screen, a series of "filtering experiments" will be performed that will include: 1) retesting of the compound to confirm its status as a "hit," 2) potency testing using dose-response experiments, 3) chemical profiling using electronic databases to filter for known toxicophores, 4) testing against a library of other RGS proteins for specificity analysis, 5) testing using a "GAP" functional assay, and 6) obtaining chemically similar compounds from commercial sources to establish structure-activity and pursue pharmacophore development.

Example 3

Figure 9A:
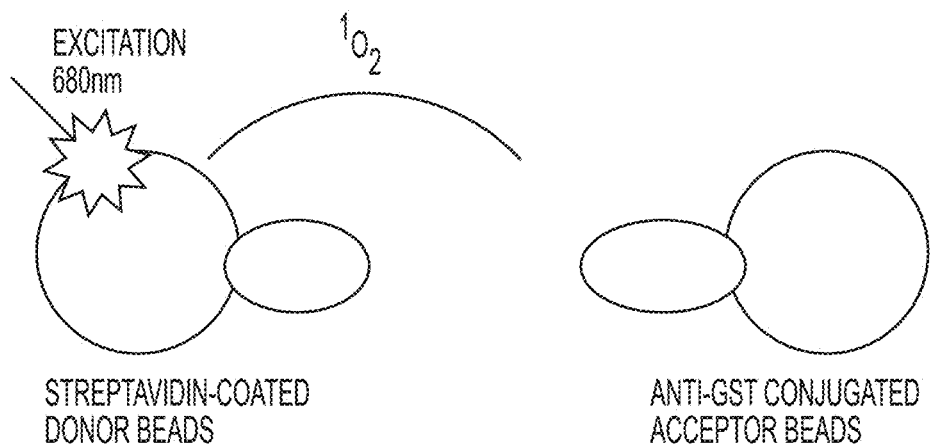
FIG. 9A-9B. Alpha screen mechanism of action. Proteins are conjugated to their respective beads. The donor bead is excited with a wavelength of 680 nm. Upon excitation, a singlet oxygen is formed from ambient oxygen, and can diffuse approximately 200 nm.
Figure 9B:
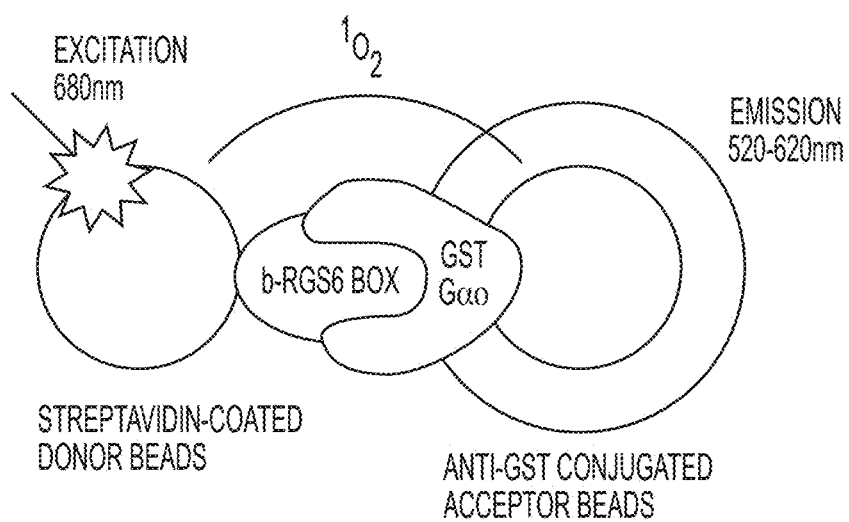

As described herein, a role for RGS6 in the regulation of alcohol dependency traits, and that inhibition of this protein may act as a therapeutic intervention for the disease of alcohol addiction. As such, 2320 compounds were screened in an initial effort to discover small molecule inhibitors of the RGS6:Gα$_o$ protein:protein interaction (ppi). Alpha screen technology was used in this screen, where both proteins are conjugated to their respective donor or acceptor beads and if a ppi exists the proximity of the beads to each other results in emission of light at 520-620 nm. If a small molecule disrupts the ppi, then the intensity of light emitted is diminished. Scheme 1, represented in FIG. 9A and FIG. 9B, shows a schematic of how alpha screen technology works. Scheme 2 shows the three most promising lead compounds from the screen.

Scheme 2: Top three hits from the Spectrum Library. IC$_{50}$ values for these compounds were determined to be: 17 μM UI1910, 49 μM UI1935, 42 μM UI1956.

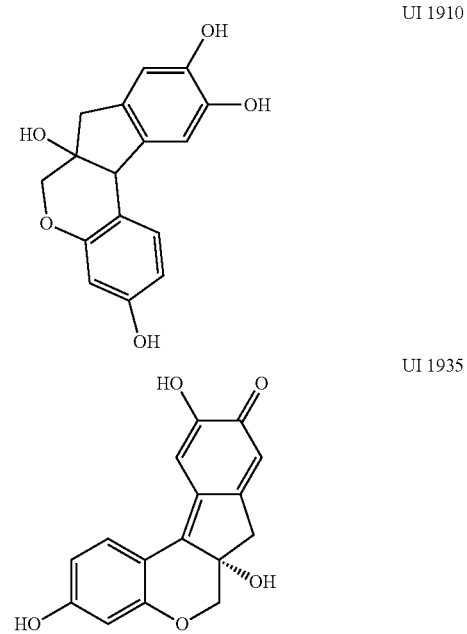

-continued

UI1956

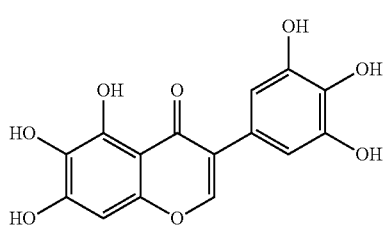

Figure 10:
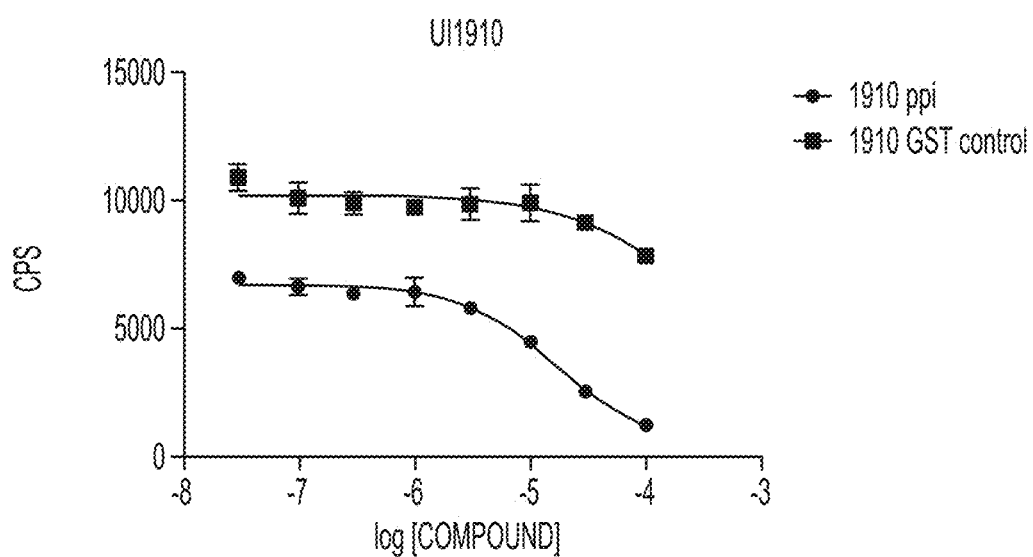
FIG. 10. Comparison of compound ability to selectively inhibit RGS6:G$\alpha_o$ ppi over the assay. UI1910 is 30 fold more selective for the ppi compared to control.
Figure 11:
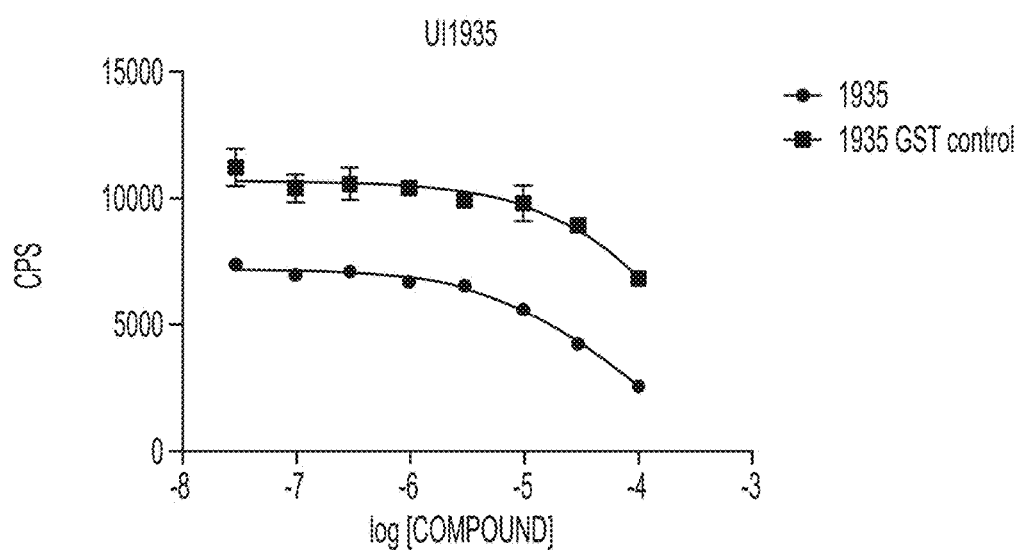
FIG. 11. Comparison of compound ability to selectively inhibit RGS6:G$\alpha_o$ ppi over the assay. UI1935, a more highly colored compound, only inhibits the ppi 5 fold more effectively than the assay.

IC$_{50}$ values were obtained from dose response experiments using Alpha Screen technology. Compounds were determined to be promising based on these IC$_{50}$ values, and based on the selectivity the compounds had for inhibiting the ppi versus inhibiting the assay. Since the Alpha Screen assay utilizes emitted light produced by singlet oxygen interacting with the acceptor bead as a determinant of ppi, highly colored compounds, or compounds that act as oxygen scavengers can produce false positive inhibition of the assay. Scheme 3, represented in FIG. 10 and FIG. 11, shows the comparison of compound inhibition of ppi vs assay for compounds UI1910 and UI1935. This was not determined for UI1956.

Finally, compounds were determined to be promising based on their selectivity for binding RGS6 over binding the G protein. This was determined via differential scanning fluorimetry (DSF). In short, as proteins are heated they become unstable and unfold. This is a characteristic of the protein and these temperatures remain constant. DSF takes advantage this trait by utilizing a dye which will only fluoresce when it comes in contact with hydrophobic regions of the protein. As such, there is a large increase in fluorescence when the protein unfolds. This assay can be used to determine compound binding because when compounds bind to proteins they will either stabilize or de-stabilize the protein causing a shift in the temperature at which the protein will unfold. Each of our compounds caused a shift in temperature for RGS6, but none was detected for the G protein, indicating that our compounds indeed disrupt the ppi by binding RGS6. (data not shown).

These data indicate that a large scale screening campaign for RGS6 inhibitors is indeed feasible. The compounds identified in this screen represent the first generation of RGS6 inhibitors. A larger screening campaign will yield molecules that are both potent and selective for inhibiting RGS6 while containing minimal reactive substructures thus cutting down on the possible side effects that reactive molecules often produce. An additional screen will utilize the full RGS6 protein. This differs from the preliminary screen above in that a truncated RGS6 construct was used for ease of purification. However, using the full-length construct will likely result in a better Alpha Screen signal due to the protein being more active. Additionally, the full-length construct contains several accessory domains that are not likely involved in the mechanism of alcohol dependence, but the binding of which may cause protein confirmation shifts resulting in disruption of the RGS:G protein ppi in an allosteric mechanism of inhibition.

All documents cited herein, including Stewart et al., Proc Natl Acad Sci USA. 2015 Feb. 17; 112(7): E786-E795 and Supporting Information, are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A method of ameliorating or alleviating the effects of ethanol consumption in an individual in need of such treatment, comprising administering to the individual an effective amount of a small molecule antagonist of Regulator of G protein Signaling 6 (RGS6), wherein the antagonist is the compound

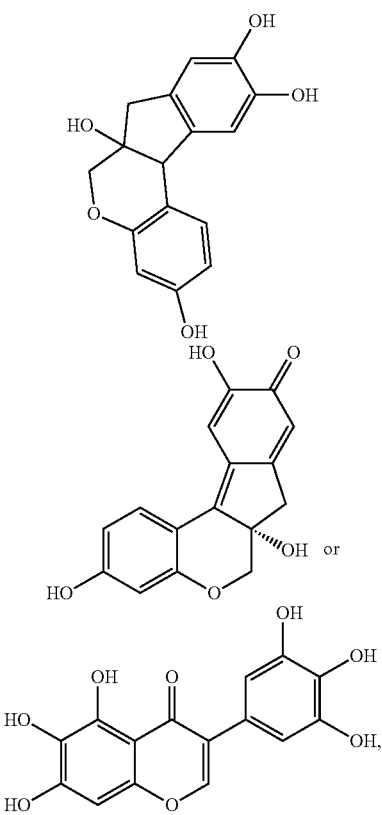

or a salt thereof.

* * * * *